United States Patent [19]

Stemp et al.

[11] Patent Number: 5,523,299
[45] Date of Patent: Jun. 4, 1996

[54] 5-(2-OXYPHENYL)-PYRROLE DERIVATIVES AS DOPAMINE $D_3$ RECEPTOR ANTAGONISTS

[75] Inventors: Geoffrey Stemp, Bishop's Stortford; Michael S. Hadley, Sawbridgeworth; David J. Nash, Little Walden; Christopher N. Johnson, Saffron Walden, all of England

[73] Assignee: SmithKline Beecham PLC, England

[21] Appl. No.: 381,838

[22] PCT Filed: Jul. 29, 1993

[86] PCT No.: PCT/EP93/02030

§ 371 Date: Feb. 3, 1995

§ 102(e) Date: Feb. 3, 1995

[87] PCT Pub. No.: WO94/03426

PCT Pub. Date: Feb. 17, 1994

[30] Foreign Application Priority Data

Aug. 6, 1992 [GB] United Kingdom ............ 9216663
May 19, 1993 [GB] United Kingdom ............ 9310317

[51] Int. Cl.$^6$ .................. C07D 207/335; C07D 401/04; C07D 401/06; C07D 403/04; C07D 403/06; A61K 31/40; A61K 31/445

[52] U.S. Cl. .......................... 514/183; 514/212; 514/216; 514/299; 514/304; 514/307; 514/326; 514/414; 514/422; 514/427; 540/480; 540/582; 540/602; 546/112; 546/122; 546/125; 546/148; 546/208; 548/465; 548/517; 548/518; 548/527; 548/560; 548/561

[58] Field of Search ...................... 540/480, 582, 540/602; 546/112, 122, 125, 148, 208; 548/465, 517, 518, 527, 560, 561; 514/183, 212, 216, 299, 304, 307, 326, 414, 422, 427

[56] References Cited

U.S. PATENT DOCUMENTS 4,785,010 11/1988 Zoller et al. ................. 514/356
4,874,770 10/1989 Van Wijngaarden et al. ...... 514/326
5,428,037 6/1995 Pascal et al. .................. 514/252

FOREIGN PATENT DOCUMENTS 0241053 10/1987 European Pat. Off. .
0259930 3/1988 European Pat. Off. .

OTHER PUBLICATIONS

Journal of Medicinal Chemistry, Ingrid Pettersson, Tommy Liljefors, 'Conformational analysis of dopamine D–2 receptor antagonists of the benzamide series in relation to a recently proposed D–2 receptor–interaction model', vol. 35(13), Jun. 26, 1992, pp. 2355–2363.

Journal of Medicinal Chemistry, Ineke Van Wijngaarden, Chris G. Kruse, Jan A. M. Van der Heyden, Martin T. M. Tulp, '2-Phenylpyrroles as conformationally restricted benzamide analogs. A new class of potential antipsychotics. 2', vol. 31, No. 10, Oct. 1988, pp. 1934–1940.

Journal of Medicinal Chemistry, Ineke Van Wijngaarden, Chris G. Kruse, Roelof Van Hes, Jan A. M. Van der Heyden, Martin T. M. Tulp, '2–Phenylpyrroles as conformationally restricted benzamide analogs. A new class of potential antipsychotics. 1', vol. 30, No. 11, 1987, pp. 2099–2104.

*Primary Examiner*—Philip I. Datlow
*Attorney, Agent, or Firm*—Nora Stein-Fernandez; Stuart R. Suter; Edward T. Lentz

[57] ABSTRACT

Compounds of formula (I),

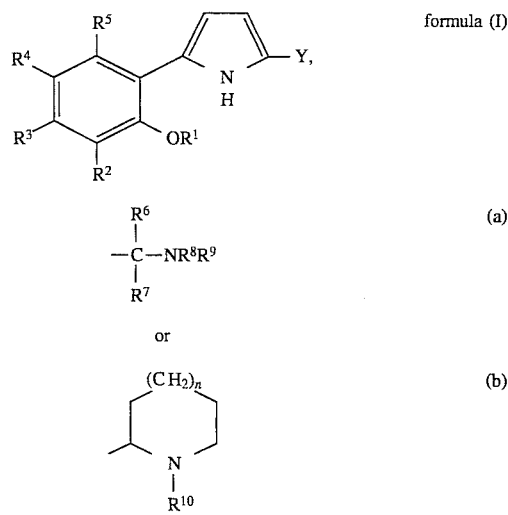

wherein $R^1$ represents $C_{1-4}$alkyl; and $R^2$, $R^3$, $R^4$ and $R^5$ each independently represent hydrogen, halogen, $C_{1-4}$alkyl, $C_{1-4}$alkoxy, $C_{1-4}$alkoxyC$_{1-4}$alkyl, $C_{1-4}$alkylsulphonyl, trifluoromethylsulphonyl; optionally substituted arylsulphonyl, optionally substituted heteroarylsulphonyl, optionally substituted aralkylsulphonyl, optionally substituted heteroaralkylsulphonyl, nitro, cyano, amino, mono- or di-alkylamino, trifluoromethyl, trifluoromethoxy, hydroxyl, hydroxyalkyl, $C_{1-4}$alkylthio, $C_{1-4}$alkanoyl, $C_{1-4}$alkoxycarbonyl, aminosulphonyl, alkylaminosulphonyl or dialkylaminosulphonyl; or $R^1$ and $R^2$ together form a linking chain–$(CH_2)_m$Op (wherein m is 2 to 4 and p is zero or 1) which chain may be optionally substituted by one or two $C_{1-4}$alkyl groups; and Y represents a group selected from (a) or (b) wherein $R^6$ and $R^7$ independently represent hydrogen, $C_{1-6}$alkyl, optionally substituted aryl$C_{1-6}$alkyl or optionally substituted heteroaryl$C_{1-6}$alkyl; $R^8$ represents $C_{1-6}$alkyl, $C_{3-6}$alkenyl or $C_{3-6}$cycloalkylC$_{1-4}$alkyl; and $R^9$ represents $C_{1-6}$alkyl; C$_{3-6}$alkenyl; $C_{3-6}$cycloalkylC$_{1-4}$alkyl, optionally substituted aryl$C_{1-4}$alkyl or optionally substituted heteroaryl$C_{1-4}$alkyl; or $NR^8R^9$ forms a heterocyclic ring (with the proviso that $NR^8R^9$ is not piperazine); $R^{10}$ represents $C_{1-6}$alkyl; $C_{3-6}$alkenyl; $C_{3-6}$cycloalkylC$_{1-4}$alkyl, optionally substituted aryl$C_{1-4}$alkyl, or optionally substituted heteroaryl$C_{1-4}$alkyl; and n is 1 to 3; and salts thereof, have affinity for dopamine $D_3$ receptors and may be useful in the treatment of e.g., psychotic disorders.

13 Claims, No Drawings

5-(2-OXYPHENYL)-PYRROLE DERIVATIVES AS DOPAMINE D₃ RECEPTOR ANTAGONISTS

This is the rational stage application at international application PCT/EP93/02030 filed Jul. 29, 1993.

The present invention relates to novel phenylpyrrole derivatives, processes for their preparation, pharmaceutical compositions containing them and their use in therapy, in particular as antipsychotic agents.

European Patent Application No. 241053, describes compounds of the formula:

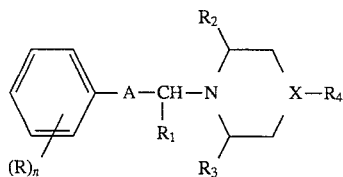

wherein A is an unsaturated 5-membered heterocyclic ring, such as 2,5-pyrrolyl, or 3,5- or 1,4- pyrazolyl; X is a nitrogen or carbon atom; $R_1$, $R_2$, $R_3$ are each hydrogen or alkyl; $R_4$ is aryl, heteroaryl, arylcarbonyl or heteroaryl-carbonyl; R is selected from a variety of substituents and n is 0–4. The compounds are said to have antipsychotic properties.

European Patent Application No. 259930 describes compounds of the formula:

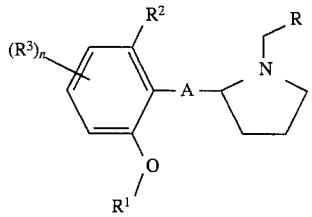

wherein A is an unsaturated 5-membered heterocyclic ring, such as 2,5-pyrrolyl, 1,4-pyrazolyl or 2,5-furyl; R is hydrogen, alkyl or optionally substituted phenyl; $R^1$ is alkyl, alkenyl or forms a ring with the phenyl group; $R^2$ is hydrogen, hydroxy or alkoxy; $R^3$ is selected from a variety of substituents and n is 0–3. These compounds are also said to have and psychotic properties.

We have now found a novel class of 2-phenylpyrroles which have high affinity for dopamine $D_3$ receptors and thus have potential as antipsychotic agents.

In a first aspect the present invention provides compounds of formula (I):

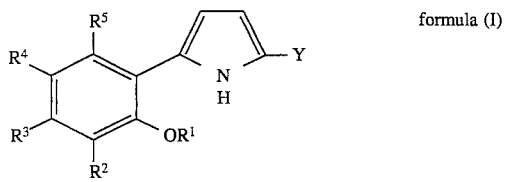

wherein $R^1$ represents $C_{1-4}$alkyl; and $R^2$, $R^3$, $R^4$ and $R^5$ each independently represent hydrogen, halogen, $C_{1-4}$alkyl, $C_{1-4}$alkoxy, $C_{1-4}$alkoxy$C_{1-4}$alkyl, $C_{1-4}$alkylsulphonyl, trifluoromethylsulphonyl; optionally substituted arylsulphonyl, optionally substituted heteroarylsulphonyl, optionally substituted aralkylsulphonyl, optionally substituted heteroalkylsulphonyl, nitro, cyano, amino, mono- or di-alkylamino, trifluoromethyl, trifluoromethoxy, hydroxyl, hydroxyalkyl, $C_{1-4}$alkylthio, $C_{1-4}$alkanoyl, $C_{1-4}$alkoxycarbonyl, aminosulphonyl, alkylaminosulphonyl or dialkylaminosulphonyl; or $R^1$ and $R^2$ together form a linking chain $-(CH_2)_mOp$; (wherein m is 2 to 4 and p is zero or 1 ) which chain may be optionally substituted by one or two $C_{1-4}$alkyl groups; and Y represents a group selected from:

or

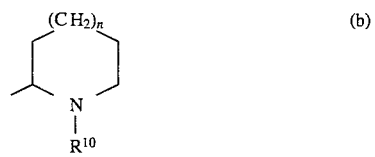

wherein $R^6$ and $R^7$ independently represent hydrogen, $C_{1-6}$alkyl, optionally substituted aryl$C_{1-6}$alkyl or optionally substituted heteroaryl$C_{1-6}$alkyl;

$R^8$ represents $C_{1-6}$alkyl, $C_{3-6}$alkenyl or $C_{3-6}$cycloalkyl$C_{1-4}$alkyl; and $R^9$ represents $C_{1-6}$alkyl; $C_{3-6}$alkenyl; $C_{3-6}$cycloalkyl$C_{1-4}$alkyl, optionally substituted aryl$C_{1-4}$alkyl or optionally substituted heteroaryl$C_{1-4}$alkyl; or $NR^8R^9$ forms a heterocyclic ting (with the proviso that $NR^8R^9$ is not piperazine);

$R^{10}$ represents $C_{1-6}$alkyl; $C_{3-6}$alkenyl; $C_{3-6}$cycloalkyl$C_{1-4}$alkyl, optionally substituted aryl$C_{1-4}$alkyl or optionally substituted heteroaryl$C_{1-4}$alkyl; and n is 1 to 3;

and salts thereof.

In the compounds of formula (I) an alkyl group or moiety may be straight or branched. Alkyl groups which may be employed include methyl, ethyl, n-propyl, isopropyl, n-butyl, t-butyl, n-pentyl; sec-pentyl, n-hexyl and the like.

Representative aryl groups or moieties present in any of the substituents $R^2$, $R^3$, $R^4$, $R^5$, $R^6$, $R^7$, $R^9$ and $R^{10}$ in compounds of formula (I) include phenyl, naphthyl, and tetrahydronaphthyl. Suitable examples of heteroaryl groups include both 5 and 6-membered heterocycles containing one or more oxygen, sulphur or nitrogen atoms, such as furyl, thienyl, pyrrolyl, oxazolyl, thiazolyl, imidazolyl, oxadiazolyl, thiadiazolyl, pyridyl, pyridazyl, pyrimidyl and pyrazyl. Substituents for said aryl and heteroaryl groups include halogen, $C_{1-4}$alkyl, $C_{1-4}$alkoxy, $C_{1-4}$alkoxyalkyl, nitro, cyano, trifluoromethyl, trifluoromethoxy, hydroxy, hydroxyalkyl, $C_{1-4}$alkanoyl, $C_{1-4}$alkoxycarbonyl, amino and mono- or -dialkylamino.

When—$NR^8R^9$ forms a heterocyclic ring, this preferably has from 4 to 10, e.g. 5 to 8 ring members, and it may be fully or partially saturated. The ring may optionally contain a sulphur atom, provided there are at least two methylene groups between the S and N atoms. A heterocyclic ring —$NR^8R^9$ may also be bridged, for example by a $C_{1-3}$alkylene chain e.g. a methylene or ethylene group. Furthermore, the heterocyclic ring may be substituted, for example by one or more $C_{1-4}$alkyl groups, or fused to an aromatic ring, such as phenyl. Representative heterocyclic groups include pyrrolidinyl, piperidinyl, 1,2,3,6-tetrahydropyridinyl, 1,2,3,4-tetrahydroisoquinolyl, hexahydroazepinyl, octahydroazocinyl, azabicyclo[3.2.1]octanyl, azabicyclo[2.2.2]octanyl, azabicylo[3.3.1]nonanyl and azabicyclo[3.2.2]nonanyl.

When $R^1$ and $R^2$ together form a group $—(CH_2)_mO_p$ wherein p is 1 it will be appreciated that the oxygen atom is attached to the phenyl ring at the $R^2$ position:

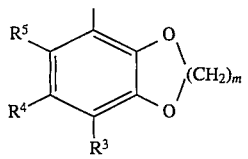

When the $(CH_2)_m$ moiety is substituted by two $C_{1-4}$alkyl groups these are preferably substituted on the same carbon atom e.g. a gem-dimethyl substituent.

$R^1$ preferably represents methyl, ethyl or isopropyl.

Preferably at least one of $R^2$ to $R^5$ is hydrogen, and the other substituents are selected from halogen, $C_{1-2}$alkyl, $C_{1-2}$alkoxy, $C_{1-2}$alkylsulphonyl, phenylsulphonyl, $CF_3$, $CF_3O$ and $C_{1-2}$dialkylaminosulphonyl.

When any of $R^2$ to $R^5$ represent halogen, this may be fluorine, chlorine; bromine or iodine.

When Y is a group (a):

$R^6$ preferably represents hydrogen;

$R^7$ preferably represents hydrogen or methyl;

$R^8$ preferably represents $C_{1-4}$alkyl and $R^9$ preferably represents $C_{1-4}$alkyl, cyclopropylmethyl, allyl or optionally substituted phenylmethyl; or $—NR^8R^9$ forms a fully or partially saturated 5 to 8 membered heterocyclic ring, optionally including a $C_{1-3}$alkylene bridge.

When Y is a group (b):

$R^{10}$ preferably represents $C_{1-4}$alkyl, cyclopropylmethyl, allyl or benzyl.

Y advantageously represents a group (a) wherein $R^6$ is hydrogen; $R^7$ is hydrogen or methyl;

$R^8$ is methyl, ethyl or propyl; and $R^9$ is methyl, ethyl, propyl, benzyl or p-methoxyphenylmethyl; or $NR^8R^9$ represents a monocyclic 5–8 membered heterocyclic ring, such as 1-pyrrolidinyl, 1-piperidinyl, 1,2,3,6-tetrahydropyridinyl, 1-hexahydroazepinyl or 1-octahydroazocinyl.

It will be appreciated that for use in medicine the salts of formula (I) should be physiologically acceptable. Suitable physiologically acceptable salts will be apparent to those skilled in the art and include for example acid addition salts formed with inorganic acids eg. hydrochloric, hydrobromic, sulphuric, nitric or phosphoric acid; and organic acids eg. succinic, maleic, acetic, fumaric, citric, tartaric, benzoic, p-toluenesulphonic, methanesulphonic or naphthalenesulphonic acid. Other non-physiologically acceptable salts eg. oxalates, may be used, for example in the isolation of compounds of formula (I) and are included within the scope of this invention. Also included within the scope of the invention are solvates and hydrates of compounds of formula (I).

When an asymmetric centre is present in a compound of formula (I) the compound will exist in the form of optical isomers (enantiomers). The present invention includes within its scope all such enantiomers and mixtures, including racemic mixtures, thereof. In addition, all possible diastereomeric forms (individual diastereomers and mixtures thereof) of compounds of formula (I) are included within the scope of the invention.

Particular compounds according to the invention include:

2-(3,5-dibromo-2-methoxyphenyl)-5-(1-piperidinylmethyl)-1H-pyrrole, 2-(5-ethylsulphonyl-2-methoxyphenyl)-5-(1-piperidinylmethyl)-1H-pyrrole, 2-(1-ethyl-2-hexahydroazepinyl)-5-(5-ethylsulphonyl-2 methoxyphenyl)-1H-pyrrole, 2-(5-chloro-2-methoxyphenyl)-5-(1-piperidinylmethyl)-1H-pyrrole, 2-(2,3-dimethoxyphenyl)-5-(1-piperidinylmethyl)-1H-pyrrole, 2-(5-ethylsulphonyl-2-methoxyphenyl)-5-[(2-(1,2,3,4-tetrahydro-isoquinolinyl))-methyl]-1H-pyrrole, 2-(5-ethylsulphonyl-2-methoxyphenyl)-5-(1-pyrrolidinylmethyl)-1H-pyrrole, 2-(5-ethylsulphonyl-2-methoxyphenyl)-5-(1-hexahydroazepinylmethyl)-1H-pyrrole, 2-(5-ethylsulphonyl-2-methoxyphenyl)-5-(1-(2-methylpiperidinyl)-methyl)-1H-pyrrole, 2-(5-ethylsulphonyl-2-methoxyphenyl)-5-(1-(cis-2,6-dimethyl-piperidinyl)methyl)-1H-pyrrole, 2-(5-ethylsulphonyl-2-methoxyphenyl)-5-(1-heptamethylene-iminylmethyl)-1H-pyrrole, 2-(5-ethylsulphonyl-2-methoxyphenyl)-5-dimethylaminomethyl-1H-pyrrole, 2-(5-ethylsulphonyl-2-methoxyphenyl)-5-dipropylaminomethyl-1H-pyrrole, 2-(5-ethylsulphonyl-2-methoxyphenyl)-5-diethylaminomethyl-1H-pyrrole, 2-(1-ethyl-2-piperidinyl)-5-(5-ethylsulphonyl-2 methoxyphenyl)-1H-pyrrole, 2-(5-ethylsulphonyl-2-methoxyphenyl)-5-[1-(1-piperidinyl)-ethyl]-1H-pyrrole, 5-(6-chloro-benzo[b]pyran-8-yl)-2-(1-piperidinylmethyl)-1H-pyrrole, 2-(3-bromo-5-ethylsulphonyl-2-methoxyphenyl)-5-(1-piperidinyl-methyl)-1H-pyrrole, 2-(3,5-dibromo-2-isopropoxyphenyl)-5-(1-piperidinylmethyl)-1H-pyrrole, 2-(3,5-dibromo-2-isopropoxyphenyl)-5-[1-(1-piperidinyl)-ethyl]-1H-pyrrole, 2-(3,5-dibromo-2-isopropoxyphenyl)-5-(N-benzyl-N-ethyl)aminomethyl-1H-pyrrole, 2-(3,5-dibromo-2-ethoxyphenyl)-5-(1-piperidinylmethyl)-1H-pyrrole, 2-(3,5-dibromo-2-ethoxyphenyl)-5-[1-(1-piperidinyl)-ethyl]-1H-pyrrole, 2-(1-(1-octahydroazocinyl)ethyl)-5-(3,5-dibromo-2-methoxyphenyl)-1H-pyrrole, 2-(3,5-dichloro-2-methoxyphenyl)-5-(1-piperidinylmethyl)-1H-pyrrole, 2-(1-(1-piperidinyl)ethyl)-5-(3,5-dibromo-2-methoxyphenyl)-1H-pyrrole, 2-(5-ethylsulphonyl-2-methoxyphenyl)-5-(N-benzyl-N-ethyl)-aminomethyl-1H-pyrrole, 2-(5-bromo-2-methoxy-3-methylphenyl)-5-(1-piperidinylmethyl)-1H-pyrrole, 2-(3-bromo-5-ethylsulphonyl-2-methoxyphenyl)-5-[1-(1-piperidinyl)-ethyl]-1H-pyrrole, 2-(3-bromo-5-ethylsulphonyl-2-methoxyphenyl)-5-(N-benzyl-N-ethyl)aminomethyl-1H-pyrrole, 2-(2-methoxy-5-trifluoromethylphenyl)-5-(1-piperidinylmethyl)-1H-pyrrole, 2-(2-methoxy-5-trifluoromethoxyphenyl)-5-(1-piperidinylmethyl)-1H-pyrrole, 2-(3,5-diiodo-2-methoxyphenyl)-5-(1-piperidinylmethyl)-1H-pyrrole, 2-(3,5-diiodo-2-methoxyphenyl)-5-[1-(1-piperidinyl)ethyl]-1H-pyrrole, 2-(2,3-dimethoxy-5-bromophenyl)-5-(1-piperidinylmethyl)-1H-pyrrole, 2-(2,3-dimethoxy-5-bromophenyl)-5-[1-(1-piperidinyl)ethyl]-1H-pyrrole, 2-(2-methoxy-5-phenylsulphonylphenyl)-5-(1-piperidinylmethyl)-1H-pyrrole, 2-(2-methoxy-5-phenylsulphonylphenyl)-5-[1-(1-piperidinyl)ethyl]-1H-pyrrole, 2-(1-benzyl-2-piperidinyl)-5-(5-ethylsulphonyl-2-methoxyphenyl)-1H-pyrrole, 2-[(8-azabicyclo[3.2.1]octan-8-yl)methyl]-5-(5-ethylsulphonyl-2-methoxyphenyl)-1H-pyrrole, 2-[(3-azabicyclo[3.2.2]nonan-3-yl)methyl]-5-(5-ethylsulphonyl-2-methoxyphenyl)- 1H-pyrrole, 2-(3,5-dibromo-2-methoxyphenyl)-5-[1-(1-hexahydroazepinyl)-ethyl]-1H-pyrrole, 2-[(2-azabicyclo[2.2.2]octan-2-yl)methyl]-5-(3,5-dibromo-2-methoxyphenyl)- 1H-pyrrole, 2-[(9-azabicyclo[3.3.1]nonan-9-yl)methyl]-5-(3,5-dibromo-2-methoxyphenyl)- 1H-pyrrole, 2-(3,5-dibromo-2-methoxyphenyl)-5-[1-(1-piperidinyl)propyl]-1H-pyrrole, 2-(N-cyclohexylmethyl-N-ethylaminomethyl)-5-(3,5-dibromo-2-methoxyphenyl)-1H-pyrrole, 2-[2-phenyl-1-(1-piperidinyl)ethyl]-5-(5-bromo-2,3-dimethoxyphenyl)-1H-pyrrole, 2-(5-ethylsulphonyl-2-methoxyphenyl)-5-[1-(1-piperidinyl)-ethyl]-1H-pyrrole, faster eluting enantiomer, and 2-(5-ethylsulphonyl-2-methoxyphenyl)-5-[1-(1-piperidinyl)-ethyl]-1H-pyrrole, slower eluting enantiomer, 2-(5-ethylsulfonyl-2-methoxyphenyl)-5-(1-(1,2,3,6-tetrahydro-pyridinyl)methyl)-1H-pyrrole, 2-(5-ethylsulfonyl-2-methoxyphenyl)-5-(1-(1-(1,2,3,6-tetrahydropyridinyl))ethyl)- 1H-pyrrole, 2-[(2-azabicyclo[3.2.1]octan-2-yl)methyl]-5-(5-ethylsulphonyl-2-methoxyphenyl)- 1H-pyrrole, 2-(5-ethylsulphonyl-2-methoxyphenyl)-5-[1-(1-pyrrolidinyl)-ethyl]-1H-pyrrole, 2-(5-ethylsulphonyl-2-methoxyphenyl)-5-[N-ethyl-N-(2-thienyl)methyl-aminomethyl]-1H-pyrrole, 2-(5-ethylsulphonyl-2-methoxyphenyl)-5-[N-ethyl-N-(2-furyl)methyl-aminoethyl]-1H-pyrrole, 2-(5-ethylsulphonyl-2-methoxyphenyl)-5-(N-benzyl-N-propyl-aminomethyl)-1H-pyrrole, 2-(3-bromo-5-ethylsulphonyl-2-methoxyphenyl)-5-[N-ethyl-N-(4-methoxyphenyl)methylaminomethyl]-1H-pyrrole, 2-(5-ethylsulphonyl-2-methoxyphenyl)-5-[N-ethyl-N-(4-methoxyphenyl)methylaminomethyl]-1H-pyrrole, 2-(5-dimethylsulphamoyl-2-methoxyphenyl)-5-[1-(piperidinyl)]methyl-1H-pyrrole, 2-[(2-azabicyclo[2.2.1]heptan-2-yl)methyl]-5-(5-ethylsulphonyl-2-methoxyphenyl)- 1H-pyrrole, 2-[(2-azabicyclo[2.2.1]hept-5-en-2-yl)methyl]-5-(5-ethylsulphonyl- 2-methoxyphenyl)-1H-pyrrole, 2-[(2-azabicyclo[3.2.1]oct-6-en-2-yl)methyl]-5-(5-ethylsulphonyl- 2-methoxyphenyl)-1H-pyrrole, 2-(2-methoxy-5-methylsulphonylphenyl)-5-(1-piperidinylmethyl)-1H-pyrrole, 2-(2,3-dimethoxy-5-ethylsulphonylphenyl)-5-(1-piperidinylmethyl)-1H-pyrrole, 2-[(3-azabicyclo[3.2.1]octan-3-yl)methyl]-5-(5-ethylsulphonyl-2-methoxyphenyl)-1H-pyrrole, 2-(5-ethylsulphonyl-2-methoxyphenyl)-5-[N-ethyl-N-[1-( 1,2,3,4-tetrahydro)naphthyl]aminomethyl]-1H-pyrrole, 2-(2-ethyl-2-azabicyclo[2.2.1]heptan-3-yl)-5-(5-ethylsulphonyl-2-methoxyphenyl)-1H-pyrrole, 2-[1-(2-azabicyclo[2.2.1]heptan-2-yl)ethyl]-5-(5-ethylsulphonyl-2-methoxyphenyl)-1H-pyrrole, 2-(5-ethylsulphonyl-2-methoxyphenyl)-5-[N-ethyl-N-(1-naphthyl)methyl-aminomethyl]-1H-pyrrole, 2-(5-isopropylsulphonyl-2-methoxyphenyl)-5-(1-piperidinylmethyl)-1H-pyrrole, (±)trans-2-(5-ethylsulphonyl-2-methoxyphenyl)-5-(perhydroisoquinolinylmethyl)-1H-pyrrole, and salts thereof.

The present invention also provides a process for preparing compounds of formula (I) which process comprises:

(a) to prepare a compound of formula (I) wherein Y is —$CH_2NR^8R^9$, carrying out a Mannich reaction with a compound of formula (II):

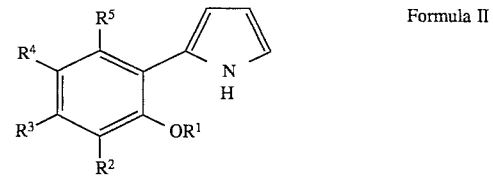

Formula II and an amine $HNR^8R^9$ in the presence of formaldehyde;

(b) to prepare compounds wherein Y is —$CHR^7NR^8R^9$ or a group of formula (b) carrying out a Vilsmeier reaction with a compound of formula (II) and an amide of formula $R^7C(O)NR^8R^9$ or a 2-oxo derivative of group (b) respectively, and reducing the intermediate product with, for example, sodium borohydride or cyanoborohydride;

(c) to prepare compounds wherein Y is —$CH_2NR^8R^9$, reductive amination of a compound of formula (III):

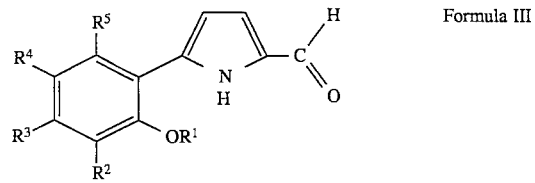

Formula III with an amine $HNR^8R^9$, and optionally thereafter forming a salt thereof.

The Mannich reaction according to process (a) may be effected according to conventional methods. Thus for example the amine $HNR^8R^9$ may first be reacted with formaldehyde and the product subsequently reacted with a compound of formula (II). The reaction is preferably effected in a protic solvent, for example an alcohol such as ethanol. An organic or inorganic acid, e.g. acetic acid may be employed as a catalyst.

The Vilsmeier reaction according to process (b) may also be effected according to conventional methods. Thus, for example, the amide $R^7C(O)NR^8R^9$ may first be reacted with phosphorus oxychloride and the resulting product subsequently reacted with a compound of formula (II). The product of this reaction is then reduced with, for example, sodium borohydride or cyanoborohydride. These reactions are preferably carried out in a non-protic solvent, for example dichloroethane or dichloromethane.

Reductive amination according to process (c) will generally be carried out using a reducing agent such as sodium borohydride or cyanoborohydride and in the presence of a Lewis acid such as titanium (IV) chloride. Reaction of a compound (III) with the amine may conveniently be effected in a solvent such as dichloromethane or dichloroethane.

A compound of formula (II) may be prepared by cyclisation of a dicarbonyl compound of formula (IV):

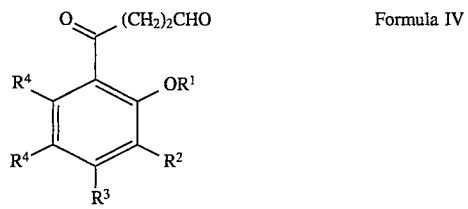

Formula IV

The reaction may be effected using an ammonium salt, e.g. ammonium acetate, in a solvent such as ethanol. (See, for example, C. G. Kruse et al., Heterocycles, vol 26, P3141, 1987).

A compound of formula (IV) may itself be prepared by reacting the appropriate substituted benzoyl halide with a metallo derivative of a 2-(2-haloethyl)-1,3-dioxolane and subsequent acid hydrolysis.

A compound of formula (III) may be prepared by carrying out a Vilsmeier reaction in which dimethylformamide is reacted with phosphorus oxychloride and the product reacted with a compound of formula (II), in a solvent such as dichloroethane, followed by acid hydrolysis.

When a compound of formula (I) is obtained as a mixture of enantiomers these may be separated by conventional methods such as crystallisation in the presence of a resolving agent, or chromatography, for example using a chiral HPLC column.

Compounds of formula (I) have been found to exhibit affinity for dopamine receptors, in particular the $D_3$ receptor and are expected to be useful in the treatment of disease states which require modulation of such receptors. Said compounds exhibit higher affinity for dopamine $D_3$ receptors than for dopamine $D_2$ receptors and may advantageously be used as selective modulators of the $D_3$ receptor. In particular compounds of formula (I) are dopamine $D_3$ receptor antagonists and as such are of potential use as antipsychotic agents for example in the treatment of schizophrenia, schizoaffective disorders, psychotic depression and mania. Other conditions which may be treated by modulation of the $D_3$ receptor include dyskinetic disorders such as Parkinson's disease, neuroleptic-induced parkinsonism and tardive dyskinesias; depression; and drug (eg. cocaine) dependency.

In a further aspect therefore the present invention provides a method of treating conditions which require modulation of the dopamine $D_3$ receptor, for example psychoses such as schizophrenia, which comprises administering to a subject in need thereof an effective mount of a compound of formula (I) or a physiologically acceptable salt thereof.

The invention also provides the use of a compound of formula (I) or a physiologically acceptable salt thereof in the manufacture of a medicament for the treatment of conditions which require modulation of the dopamine $D_3$ receptor, for example psychoses such as schizophrenia.

For use in medicine, the compounds of the present invention are usually administered as a standard pharmaceutical composition. The present invention therefore provides in a further aspect pharmaceutical compositions comprising a novel compound of formula (I) or a physiologically acceptable salt thereof and a physiologically acceptable carrier.

The compounds of formula (I) may be administered by any convenient method, for example by oral, parenteral, buccal, sublingual, nasal, rectal or transdermal administration and the pharmaceutical compositions adapted accordingly.

The compounds of formula (I) and their physiologically acceptable salts which are active when given orally can be formulated as liquids or solids, for example syrups, suspensions or emulsions, tablets, capsules and lozenges.

A liquid formulation will generally consist of a suspension or solution of the compound or physiologically acceptable salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard careers and then fried into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or physiologically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantifies in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

Preferably the composition is in unit dose form such as a tablet, capsule or ampoule.

Each dosage unit for oral administration contains preferably from 1 to 250 mg (and for parenteral administration contains preferably from 0.1 to 25 mg) of a compound of the formula (I) or a physiologically acceptable salt thereof calculated as the free base.

The physiologically acceptable compounds of the invention will normally be administered in a daily dosage regimen (for an adult patient) of, for example, an oral dose of between 1 mg and 500 mg, preferably between 10 mg and 400 mg,e.g. between 10 and 250 mg or an intravenous, subcutaneous, or intramuscular dose of between 0.1 mg and 100 mg, preferably between 0.1 mg and 50 mg, e.g. between 1 and 25 mg of the compound of the formula (I) or a physiologically acceptable salt thereof calculated as the free base, the compound being administered 1 to 4 times per day. Suitably the compounds will be administered for a period of continuous therapy, for example for a week or more.

The invention is further illustrated by the following non-limiting examples:

DESCRIPTION 1

(3-Bromo-5-ethylsulphonyl-2-hydroxy)benzoic acid (D1)

A mixture of (5-ethylsulphonyl-2-methoxy)benzoic acid (10 g, 41 mmol), bromine (21 ml, 408 mmol) and 49% hydrogen bromide in acetic acid (1 ml) in glacial acetic acid (200 ml) was heated at 75° C. for 5 days. The mixture was cooled and the glacial acetic acid removed in vacuo. The residue was triturated with water (4×400 ml) and the resultant solid dried to afford the title compound (D1) (11.5 g).

NMR $\delta$(CDCl$_3$) 1.3 (3H, t, J=7 Hz), 3.2 (2H, q, J=7 Hz), 8.25 (1H, d, J=2 Hz), 8.45 (1H, d, J=2 Hz), 12.0 (1H, br s).

DESCRIPTION 2

(3-Bromo-5-ethylsulphonyl-2-methoxy)benzoic acid (D2)

Dimethyl sulphate (10.8 g, 85.6 mmol) was added dropwise to a stirred mixture of (3-bromo-5-ethylsulphonyl-2-hydroxy)benzoic acid (D1) (11.5 g, 37.2 mmol) and potassium carbonate (11.3 g, 82 mmol) in AR acetone (200 ml). On complete addition the mixture was heated at reflux for 18 h before being cooled to ambient temperature. The mixture was filtered and the filter cake washed with fresh acetone. Combined filtrates were evaporated in vacuo to afford a brown oil. This was dissolved in MeOH (200 ml), aqueous NaOH (40%, 4.3 ml) added and the mixture stirred at reflux for 1.5 h. On cooling the mixture was concentrated in vacuo and the residue partitioned between diethyl ether and water. The aqueous layer was washed with diethyl ether (100 ml), acidified with 5 N HCl and extracted with dichloromethane (3×150 ml). The combined dichloromethane extracts were dried (Na$_2$SO$_4$) and the solvent evaporated in vacuo to give the rifle compound (D2) (12 g) which could be recrystallised from ethyl acetate - pentane.

NMR $\delta$(CDCl$_3$) 1.3 (3H, t, J=7 Hz), 3.2 (2H, q, J=7 Hz), 4.1 (3H, s), 8.3 (1H, d, J=2 Hz), 8.45 (1H, d, J=2 Hz).

DESCRIPTION 3

(3-Bromo-5-ethylsulphonyl-2-methoxy)benzoyl chloride (D3)

(3-Bromo-5-ethylsulphonyl-2-methoxy)benzoic acid (D2) (6.84 g, 21 mmol) was added portionwise to thionyl chloride (40 ml) with stirring and the resultant solution stirred at reflux for 2.5 h. On cooling the solution was evaporated in vacuo, the residue treated with dry toluene (100 ml) and evaporated in vacuo to give the title compound (D3) (6.85 g).

NMR $\delta$ (CDCl$_3$) 1.35 (3H, t, J=7 Hz), 3.2 (2H, q, J=7 Hz), 4.0 (3H, s), 8.3 (1H, d, J=2 Hz), 8.4 (1H, d, J=2 Hz).

DESCRIPTION 4

2-(3-Bromo-5-ethylsulphonyl-2-methoxyphenyl)-1H-pyrrole (D4)

Formed from (3-bromo-5-ethylsulphonyl-2-methoxy)benzoyl chloride (D3) (5.3 g) by the method of Kruse et al (Heterocycles, 26, 3141, 1987).

NMR $\delta$(CDCl$_3$) 1.3 (3H, t, J=7 Hz), 3.2 (2H, t, J=7 Hz), 3.8 (3H, s), 6.35 (1H, m), 6.75 (1H, m). 6.95 (1H, m), 7.9 (1H, d, J=7 Hz), 8.05 (1H, d, J=7 Hz), 9.6 (1H, br s).

DESCRIPTION 5

(3,5-Dibromo-2-isopropoxy)benzoic acid (D5)

To a solution of (3,5-Dibromo-2-hydroxy)benzoic acid (11.1 g) in dry DMF (80 ml), was added anhydrous potassium carbonate (24 g) with stirring. Isopropyl iodide (17.5 ml) was added in one portion and the mixture was stirred at room temperature for two days. The mixture was then heated to 70° C. for 24 hrs. After cooling, the mixture was partitioned between water (150 ml) and ethyl acetate (500 ml). The organic layer was washed with brine and dried over sodium sulphate. Removal of the solvent gave a solid gum that was dissolved in dichloromethane. The mixture was filtered and the solvent was evaporated in vacuo to give a pale yellow oil (8.4 g). A portion of this oil (7.1 g) was dissolved in EtOH (100 ml) and a solution of NaOH (2.35 g) in water (35 ml) was added. The mixture was heated to reflux. After 3 hrs, the mixture was cooled and partitioned between diethyl ether (100 ml) and water (150 ml). The aqueous layer was brought to pH 1 with 5 M HCl and was extracted with dichloromethane (3×100 ml). The combined dichloromethane layers were dried over sodium sulphate and evaporated in vacuo to give the title compound (D5), (5.75g).

NMR $\delta$(CDCl$_3$) 1.4 (6H, d, J=6 Hz), 4.9 (1H, septet, J=6 Hz), 7.9 (1H, d, J=2 Hz), 8.2 (1H, d, J=2 Hz).

Analysis: Found C, 35.44, H, 2.97%; $C_{10}H_{10}O_3Br_2$ requires C, 35.54, H, 2.98%.

DESCRIPTION 6

(3,5-Dibromo-2-isopropoxy)benzoyl chloride (D6)

To a slurry of (3,5-Dibromo-2-isopropoxy)benzoic acid (D5) (5.75 g) in dry toluene (18 ml) was added oxalyl chloride (3.0 ml) at room temperature. A drop of DMF was added and the mixture was stirred at room temperature for 2 hrs. The mixture was evaporated in vacuo and dissolved in dry toluene (50 ml). The toluene was decanted off and evaporated in vacuo to give the title compound (D6), (5.7 g).

NMR $\delta$(CDCl$_3$) 1.3 (6H, d, J=6 Hz), 4.5 (1H, septet, J=6 Hz), 7.9 (1H, d J=2 Hz), 8.0 (1H, d, J=2 Hz).

DESCRIPTION 7

2-(3,5-Dibromo-2-isopropoxyphenyl)-1H-pyrrole (D7)

Formed from (3,5-Dibromo-2-isopropoxy)benzoyl chloride (D6) by the method of Kruse et al., (Heterocycles, 26, 3141, 1987).

NMR $\delta$(CDCl$_3$) 1.2 (6H, d, J=7 Hz), 4.4 (1H, septet, J=7 Hz), 6.3 (1H, m) 6.5 (1H, m), 6.9 (1H, m), 7.5 (1H, d, J=3 Hz), 7.6 (1H, d, J=3 Hz), 9.5 (1H, m).

Analysis: Found C, 43.57, H, 3.59, N, 3.63%; $C_{13}H_{13}NOBr_2$ requires C, 43.49, H, 3.65, N, 3.90%.

DESCRIPTION 8

2-(3,5-Dibromo-2-ethoxyphenyl)-1H-pyrrole (D8)

This material was formed by methods analogous to those of description 2, using diethyl sulphate and (3,5-dibromo-2-hydroxy)benzoic acid to give (3,5-dibromo-2-ethoxy)benzoic acid which was further treated using the methods of descriptions 6 and 7.

NMR δ(CDCl$_3$) 1.4 (3H, t, J=6 Hz), 3.9 (2H, q, J=6 Hz), 6.3 (1H, m), 6.6 (1H, m), 6.9 (1H, m), 7.5 (1H, d, J=2 Hz), 7.7(1H, d, J=2 Hz).

Analysis: Found C, 41.96, H, 3.36, N, 3.72%; C$_{12}$H$_{11}$NOBr$_2$ requires C, 41.77, H, 3.21, N, 4.06%.

DESCRIPTION 9

1-Acetyloctahydroazocine (D9)

To a stirred solution of heptamethyleneimine (5.56 ml; 44 mmol) and triethylamine (6.13 ml; 44 mmol) in tetrahydrofuran (20 ml) under nitrogen at 0° C. was added dropwise a solution of acetyl chloride (3.13 ml; 44 retool) in tetrahydrofuran (20 ml). The reaction mixture was then warmed to room temperature and stirred for 1 hr. The resulting solid was filtered off and washed thoroughly with ether. The filtrate was evaporated in vacuo to give an orange oil. Distillation in vacuo gave the title compound (D9).

NMR δ(CDCl$_3$) 1.52 (6H, m), 1.71 (4H, m), 2.08 (3H, s), 3.39 (2H, t, J=6 Hz), 3.45 (2H, t, J=6 Hz).

DESCRIPTION 10

2-(3,5-Dibromo-2-methoxyphenyl)-1H-pyrrole (D10)

Prepared by methods analogous to those of descriptions 2, 3 and 4, starting from (3,5-dibromo-2-hydroxy)benzoic acid.

NMR δ(CDCl$_3$) 3.75 (3H, s), 6.32 (1H, m), 6.60 (1H, m), 6.93 (1H, m), 7.49 (1H, d, J=2 Hz), 7.65 (1H, d, J=2 Hz), 9.63 (1H, br s).

DESCRIPTION 11

2-(3,5-Dichloro-2-methoxyphenyl)-1H-pyrrole (D11)

Prepared by methods analogous to those of descriptions 2, 3 and 4, starting from (3,5-dichloro-2-hydroxy)benzoic acid.

NMR δ(CDCl$_3$) 3.78 (3H, s), 6.30 (1H, q, J=3 Hz), 6.61 (1H, m), 6.93 ( 1H, m), 7.17 (1H, d, J=2Hz), 7.47 (1H, d, J=2Hz), 9.17 (1H, br s).

DESCRIPTION 12

(5-Bromo-2-methoxy-3-methyl)benzoic acid (D12)

To a stirred suspension of 3-methylsalicylic acid (10 g, 66 mmol) in glacial acetic acid (100 ml) at room temperature was added bromine (3.5 ml; 69 mmol). The reaction mixture was stirred at room temperature for 3 hrs, and the resulting solid filtered off to give the title compound (D12).

NMR δ(CDCl$_3$) 2.15 (3H, s), 7.49 (1H, d, J=2 Hz), 7.69 (1H, d, J=2 Hz), 11.55 (1H, br s).

DESCRIPTION 13

2-(5-Bromo-3-methyl-2-methoxyphenyl)-1H-pyrrole (D13)

Prepared by methods analogous to those of descriptions 2, 3 and 4, starting from (5-bromo-3-methyl- 2-hydroxy)benzoic acid (D 12).

NMR δ(CDCl$_3$) 2.30 (3H,s), 3.53 (3H,s), 6.28 1H, q, J=2 Hz), 6.56 (1H, m), 6.88 (1H, m), 7.22 (1H, d, J=1.5 Hz), 7.54 (1H, d, J=1.5 Hz), 9.65 (1H, br s).

DESCRIPTION 14

(4-Trifluoromethyl)anisole (D14)

Dimethyl sulphate (8.96 g, 70 mmol) was added dropwise to a stirred mixture of (4-trifluoromethyl)phenol (10 g, 62 mmol) and potassium carbonate (9.4 g, 68 mmol) in AR acetone (200 ml) and the resultant mixture stirred at reflux for 4 h. The mixture was cooled and filtered and the filter cake washed with fresh acetone. Combined filtrates were evaporated in vacuo to afford the title compound (D14) (10 g).

NMR δ(CDCl$_3$) 3.85 (3H, s), 6.9 (2H, d, J=8 Hz), 7.5 (2H, d, J=8 Hz).

DESCRIPTION 15

(2-Methoxy-5-trifluoromethyl)benzoic acid (D15)

The reaction was carried out under a nitrogen atmosphere. To a solution of n-butyllithim (1.6M in hexanes; 71 ml) in hexane (200 ml) at ambient temperature was added tetramethylethylenediamine (17.15 ml, 114 mmol) dropwise with stirring. To this mixture was added (4-trifluoromethyl)anisole (D14) (10 g, 56.8 mmol) in hexane (50 ml) dropwise. After 1.5 h the mixture was poured onto solid carbon dioxide. Water was added and the aqueous layer separated and washed with diethyl ether (200 ml). The aqueous layer was acidified with 5 N HCl and extracted with dichloromethane (3×200 ml). Combined halogenated organic extracts were dried (Na$_2$SO$_4$) and evaporated in vacuo to afford the title compound (D15) (7.53 g).

NMR δ(CDCl$_3$) 4.1 (3H, s), 7.15 (1H, d, J=8 Hz), 7.8 (1H, dd, J=8 Hz, 1 Hz), 8.4 (1H, d, J=1Hz).

DESCRIPTION 16

(2-Methoxy-5-trifluoromethyl)benzoylchloride (D16)

Prepared from (2-methoxy-5-trifluoromethyl)benzoic acid (D15) (5 g) by the method of description 3.

NMR δ(CDCl$_3$) 4.0 (3H, s), 7.1 (1H, d, J=8 Hz), 7.8 (1H, dd, J=8 Hz, 2 Hz), 8.3 (1 H, d, J=2 Hz).

DESCRIPTION 17

2-(2-Methoxy-5-trifluoromethylphenyl)-1H-pyrrole (D17)

Prepared from (2-methoxy-5-trifluoromethyl)benzoyl chloride (D16) (5.2 g) by the method of Kruse et al (Heterocycles, 26,3141,1987).

NMR δ(CDCl$_3$) 4.0 (3H, s), 6.3 (1H, m), 6.7 (1H, m), 6.9 (1H, m), 7.0 (1H, d, J=8 Hz), 7.4 (1H, dd, J=8 Hz, 2 Hz), 7.8 (1H, d, J=2 Hz), 9.8 (1H, br s).

DESCRIPTION 18

(2-Hydroxy-5-trifluoromethoxy)benzoic acid (D18)

Aqueous AgNO$_3$ (25%; 1.65 ml) and aqueous NaOH (25%; 0.39 ml) were mixed with stirring and the precipitated AgO filtered and washed with water. The AgO was covered with water and stirred as NaOH (0.5 g) was added in one portion. Once the NaOH had dissolved (2-hydroxy-5-trifluoromethoxy)benzaldehyde (0.5 g) was added and the mixture stirred for 1 h. The mixture was filtered and the filtrate acidified with 5 N HCl and extracted with dichloromethane (3×50 ml). Combined organic extracts were dried (Na$_2$SO$_4$) and evaporated in vacuo to give the title compound (D18) (0.39 g).

NMR δ(CDCl$_3$) 7.0 (1H, d, J=8 Hz), 7.4 (1H, dd, J=8 Hz, 2 Hz), 7.8 (1H, d, J=2 Hz), 10.3 (1H, s).

DESCRIPTION 19

2-(2-Methoxy-5-trifluoromethoxyphenyl)-1H-pyrrole (D19)

Prepared by methods analogous to those of descriptions 2, 3 and 4, starting from (2-hydroxy- 5-trifluoromethoxy)benzoic acid (D18).

NMR δ(CDCl$_3$) 4.0 (3H, s), 6.3 (1H, m), 6.55 (1H, m), 6.9–7.1 (3H, m), 7.5 (1H, d, J=2 Hz), 9.8 (1H, br s).

DESCRIPTION 20

2-(3,5-Diiodo-2-methoxyphenyl)-1H-pyrrole (D20)

Prepared by methods analogous to those of descriptions 2, 3 and 4, starting from (3,5-diiodo-2-hydroxy)benzoic acid.

NMR δ(CDCl$_3$) 3.7 (3H, s), 6.3 (1H, m), 6.6 (1H, m), 6.9 (1H, m), 7.85 (1H, d, J=2 Hz), 7.9 (1H, d, J=2 Hz).

DESCRIPTION 21

(5-Bromo-2,3-dihydroxy)benzoic acid (D21)

Bromine (40 ml, 779 mmol) was added dropwise to a stirred solution of 2,3-dihydroxybenzoic acid (120 g, 779 mmol) in glacial acetic acid (900 ml) at ambient temperature. After 24 h the mixture was evaporated in vacuo and the residue recrystallised from MeOH—H$_2$O (9:1) to give the title compound (D21) (150 g).

NMR δ(CDCl$_3$) 7.2 (1H, d, J=2 Hz), 7.4 (1H, d, J=2 Hz), 10.0 (1H, br m).

DESCRIPTION 22

2-(2,3-Dimethoxy-5-bromophenyl)-1H-pyrrole (D22)

Prepared by methods analogous to those of descriptions 2, 3 and 4, starting from (5-bromo-2,3-dihydroxy)benzoic acid (D21 ) and using 3 equivalents of dimethyl sulphate.

NMR δ(CDCl$_3$) 3.9 (6H, s), 6.3 (1H, m), 6.6 (1H, m), 6.8 (1H, d, J=2 Hz,),6.9 (1H, m), 7.35 (1H, m), 9.8 (1H, br m).

DESCRIPTION 23

(2-Phenylsulphonyloxy)benzoic acid methyl ester (D23)

Phenylsulphonyl chloride (17.7 g, 100 mmol) was added dropwise at ambient temperature to a stirred solution of methyl salicylate (15.2 g, 100 mmol) and triethylamine (14 ml, 100 mmol) in dichloromethane (300 ml). After 2 h the mixture was evaporated in vacuo and the residue partitioned between ether and water. The organic layer was washed with water, dried (Na$_2$SO$_4$) and evaporated in vacuo. The crude material was purified by chromatography on silica gel using ether - pentane to afford the title compound (D23).

NMR δ(CDCl$_3$) 3.8 (3H, s), 7.0–8.0 (8H, m).

DESCRIPTION 24

(2-Methoxy-5-phenylsulphonyl)benzoic acid (D24)

(2-Phenylsulphonyloxy)benzoic acid methyl ester (D23) (20.3 g, 69.5 mmol) and aluminium chloride (18.6 g, 139 mmol) were stirred together at 140° C. for 1.25 h. The mixture was allowed to cool and stirred with concentrated HCl (150 ml) and ice (50 g). The product was extracted into dichloromethane (3×200 ml) and the combined extracts dried (Na$_2$SO$_4$) and evaporated in vacuo. The residue was dissolved in AR acetone (250 ml) and potassium carbonate (19.2 g, 139 mmol) added. To this mixture was added dimethyl sulphate (13 ml, 137 mmol) dropwise and the resultant mixture heated at reflux for 21 h. The cooled mixture was filtered and the filter cake washed with fresh acetone. Combined filtrates were evaporated in vacuo and the residue treated with water (250 ml) and NaOH (40%; 12.7 ml). The mixture was heated at reflux for 3 h. The solution was cooled and washed with dichloromethane. The aqueous layer was acidified with concentrated HCl and extracted with dichloromethane (2×150 ml). Combined extracts were dried (Na$_2$SO$_4$) and evaporated in vacuo to give the title compound (D24) (8.8 g).

NMR δ(CDCl$_3$) 4.1 (3H, s), 7.15 (2H, d, J=8 Hz), 7.4–7.7 (3H, m), 7.95 ( 2H, m), 8.2 (1H, dd, J=8 Hz, 2 Hz), 8.65 (1H, d, J=2 Hz).

DESCRIPTION 25

2-(2-Methoxy-5-phenylsulphonylphenyl)-1H-pyrrole (D25)

Prepared by methods analogous to those of descriptions 3 and 4, starting from (2-methoxy-5-phenylsulphonyl)benzoic acid (D24).

NMR δ(CDCl$_3$) 4.0 (3H, s), 6.3 (1H, m), 6.75 (1H, m), 6.9 (1H, m), 7.0 (1H, d, J=8 Hz), 7.4–7.6 (3H, m), 7.7 (1H, dd, J=8 Hz, 2 Hz), 7.95 (2H, dd, J=8 Hz, 2 Hz), 8.2 (1H, d, J=2 Hz), 9.7 (1H, br s).

DESCRIPTION 26

N-Benzyl-2-piperidinone (D26)

To a suspension of sodium hydride (80%, 3.3 g, 0.11 mol) in dry toluene (250 ml) under argon, was added dropwise a solution of δ-valerolactam (9.9 g, 0.10 mol) in toluene (50 ml). When the addition was complete, the mixture was heated under reflux for 1 h, then cooled to ambient temperature. A solution of benzyl bromide (13 ml, 18.8 g, 0.11 mol) in toluene (50 ml) containing dimethyl formamide (1 ml) was then added dropwise over 15 minutes. The resulting mixture was heated under reflux for 4 h. On cooling, the mixture was filtered and the filtrate was dried (Na$_2$SO$_4$) and evaporated in vacuo to give an oil. Bulb-to-bulb distillation gave the title compound (D26) as a yellow oil (8.0 g).

NMR δ(CDCl$_3$) 1.75 (4H, m), 2.46 (2H, t, J=6 Hz), 3.19 (2H, t, J=6 Hz), 4.60 (2H, s) and 7.29 (5H, m).

DESCRIPTION 27

1-Acetylhexahydroazepine (D27)

This compound was prepared by a method analogous to that of description 9 using hexamethyleneimine in place of heptamethyleneimine.

NMR δ(CDCl$_3$) 1.58 (4H, m), 1.78 (4H, m), 2.10 (3H, s), 3.45 (2 H, t, J=6 Hz), 3.55 (2H, t, J=6 Hz).

DESCRIPTION 28

1-Propionylpiperidine (D28)

This compound was prepared by a method analogous to that of description 9 using piperidine in place of heptamethyleneimine and propionyl chloride in place of acetyl chloride.

NMR δ(CDCl$_3$) 1.15 (3H, t, J=7 Hz), 1.58 (6H, m), 2.35 (2H, q, J=7 Hz), 3.40 (2H, t, J=6 Hz), 3.55 (2H, t, J=6 Hz).

DESCRIPTION 29

5-(3,5-Dibromo-2-methoxyphenyl)-1H-pyrrole-2-carboxaldehyde (D29)

Phosphorus oxychloride (0.18 ml, 1.9 mmol) was added to N,N-dimethylformamide (0.15 ml, 1.9 mmol) at 0° C. under argon with constant stirring. The resulting mixture was allowed to warm to room temperature and was then stirred for 1.5 h. 1,2-Dichloroethane (1.5 ml) was added and a solution of 2-(3,5-dibromo-2-methoxyphenyl)-1H-pyrrole (0.30 g, 0.91 mmol) in 1,2-dichloroethane (3 ml) was then added at 0° C. The reaction mixture was stirred at room temperature for 16 h. On cooling, the mixture was poured onto crushed ice and basified with aqueous sodium acetate (50%, 20 ml). The organic phase was separated and the aqueous layer was extracted with ether. The combined organic extracts were washed with aqueous sodium hydrogen carbonate, dried ($Na_2SO_4$) and evaporated in vacuo to give an oil. Chromatography on alumina (Brockmann grade 1) with ether - methanol (0–1%) gradient elution gave the title compound (D29) as a beige solid (0.18 g).

NMR δ($CDCl_3$) 3.80 (3H, s), 6.70 (1H, m), 7.00 (1H, m), 7.65 (1H, d, J=3Hz), 7.70 (1H, d, J=3 Hz), 9.60 (1H, s), 10.35 (1H, br s).

DESCRIPTION 30

(N-Cyclohexylmethyl)acetamide (D30)

This compound was prepared by a method analogous to that of description 9 using cyclohexanemethylamine in place of heptamethyleneimine.

NMR δ0.95 (2H, m), 1.23 (4H, m), 1.46 (1H, m), 1.70 (4H, m), 2.00 (3H, s), 3.10 (2H, t, J=6 Hz), 5.62 (1H, br s).

DESCRIPTION 31

N-Ethylcyclohexanemethylamine (D31)

To a stirred suspension of lithium aluminium hydride (0.49 g, 12 mmol) in dry tetrahydrofuran (50 ml) under argon was added a solution of (N-Cyclohexylmethyl)acetamide (D30) (2.05 g, 11 mmol) in tetrahydrofuran (50 ml) dropwise at 0° C. The resulting mixture was then heated under reflux for 2.5 h. On cooling, the excess lithium aluminium hydride was decomposed with methanol (2.5 ml) and water (24 ml) and the mixture was then extracted with dichloromethane. The combined organic extracts were acidified with 5N HCl and the aqueous layer then treated with sodium hydrogen carbonate. The basic solution was extracted with dichloromethane and the organic extracts were dried ($Na_2SO_4$) and evaporated in vacuo to afford the title compound (D31) as a yellow oil (1.40 g).

NMR δ0.92 (2H, m), 1.10 (3H, t, J=7 Hz), 1.25 (4H, m), 1.45 (1H, m), 1.70 (4H, m), 2.43 (2H, d, J=6 Hz), 2.62 (2H, q, J=7 Hz).

DESCRIPTION 32

1-(1-Phenylacetyl)piperidine (D32)

This compound was prepared by a method analogous to that of description 9 using piperidine in place of heptamethyleneimine and phenylacetyl chloride in place of acetyl chloride.

NMR δ($CDCl_3$) 1.35 (2H, m), 1.55 (4H, m), 3.35 (2H, t, J=6 Hz), 3.60 (2H, t, J=6 Hz), 3.73 (2H, s), 7.28 (5H, m).

DESCRIPTION 33

1-Acetyl-1,2,3,6-tetrahydropyridine (D33)

This compound was prepared by a method analogous to that of description 9 using 1,2,3,6-tetrahydropyridine in place of heptamethyleneimine. b.p. 95°–105° C. at 0.5 mm Hg

DESCRIPTION 34

N-Acetyl-2-pyrrolidinone (D34)

This compound was prepared by a method analogous to that of description 9 using pyrrolidine in place of heptamethyleneimine.

NMR δ($CDCl_3$) 1.90 (4H, m), 2.05 (3H, s) and 3.45 (4H, m).

DESCRIPTION 35

5-(3-Bromo-5-ethylsulphonyl-2-methoxyphenyl)-1H-pyrrole-2-carboxaldehyde (D35)

This compound was prepared by a method analogous to that of description 29, but using 2-(3-bromo-5-ethylsulphonyl-2-methoxyphenyl)-1H-pyrrole in place of 2-(3,5-dibromo-2-methoxyphenyl)-1H-pyrrole.

NMR δ($CDCl_3$) 1.34 (3H, t, J=7 Hz), 3.19 (2H, q, J=7 Hz), 3.88 (3H, s), 6.84 (1H, dd, J=4 Hz and 3 Hz), 7.05 (1H, dd, J=4 Hz and 3 Hz), 8.04 (1H, d, J=2 Hz), 8.14 (1 H, d, J=2 Hz), 9.61 (1H, s) and 10.48 (1H, br. s).

EXAMPLE 1

2-(3,5-Dibromo-2-methoxyphenyl)-5-(1-piperidinylmethyl)-1H-pyrrole hydrochloride (E1)

A solution of piperidine (0.10 ml; 1 mmol) in ethanol (20 ml) at room temperature was treated with aqueous formaldehyde (40%; 0.075 ml; 1 mmol) and glacial acetic acid (0.08 g, 1 mmol). The mixture was stirred at room temperature for 30 mins then was added dropwise to a solution of 2-(3,5-dibromo-2-methoxyphenyl)-1H-pyrrole (0.25 g, 0.75 mmol) in ethanol (20 ml). The reaction mixture was stirred at room temperature for 18 hours then evaporated in vacuo. Chromatography on alumina (Brockmann grade 1) with ether - methanol (0–2%) gradient elution gave an oil (0.23 g), which was dissolved in ether and the solution washed with water (5×50 ml). The solution was extracted with hydrochloric acid (0.1M; 3×30 ml), the combined aqueous extracts were extracted with dichloromethane (3×30 ml), and the combined organic extracts were dried over anhydrous sodium sulphate and evaporated in vacuo to give the title compound (E1) as a white foam (0.13 g, 37%).

Mass spectrum: Found $M^+$427.9942; $C_{17}H_{20}Br_2N_2O$ requires $M^+$427.9861

EXAMPLE 2

2-(5-Ethylsulphonyl-2-methoxyphenyl)-5-(1-piperidinylmethyl)-1H-pyrrole (E2)

A solution of piperidine (0.027 g, 0.32 mmol) in dry ethanol (2 ml) at room temperature was treated with aqueous formaldehyde (40%; 0.030g, 0.34 mmol) and glacial acetic acid (0.027 g, 0.45 mmol). The mixture was stirred at room temperature for 30 mins then was added dropwise to a solution of 2-(5-ethylsulphonyl-2-methoxyphenyl)-1H-pyrrole (0.086 g, 0.32 mmol) in dry ethanol (1 ml). The reaction mixture was stirred at room temperature for 18 hours then evaporated in vacuo. Chromatography on alumina (Brockmann grade 1) with ethyl acetate as eluant gave the title compound (E2) as a waxy solid after trituration with pentane (0.082 g, 70%).

NMR δ($CDCl_3$) 1.25 (3H, t, J=7 Hz), 1.46 (2H, m), 1.58 (4H, m), 2.40 (4H, m), 3.11 (2H, q, J=7 Hz), 3.51 (2H, s), 4.05 (3H, s), 6.08 (1H, t, J=2 Hz), 6.63 (1H, t, J=2 Hz), 7.05 (1H, d, J=10 Hz), 7.64 (1H, dd, J=10, 2 Hz), 8.08 (1H, d, J=2 Hz), 9.80 (1H, br s).

Mass spectrum: $^m$/z 362 ($M^+$, 25%), 278 (100)

EXAMPLE 3

2-(1-Ethyl-2-hexahydroazepinyl)-5-(5-ethylsulphonyl-2-methoxyphenyl)-1H-pyrrole hydrochloride (E3)

Phosphorus oxychloride (0.135 ml; 1.5 mmol) was added to 1-ethylhexahydroazepin-2-one (0.212 g, 1.5 mmol) at room temperature under nitrogen with constant stirring. The resulting mixture was stirred at room temperature for 30 mins then dichloroethane (30 ml) was added. The reaction mixture was cooled to 5° C., then 2-(5-ethylsulphonyl-2-methoxyphenyl)-1H-pyrrole (0.265 g, 1 mmol) was added portionwise. The reaction mixture was stirred at 5° C. for 2 hours, then at room temperature for 48 hours. Sodium borohydride (0.34 g, 8.9 mmol) was added portionwise with ice cooling, and stirring at room temperature was carried out for 3 hours. The mixture was cooled to 5° C. and treated dropwise with water (1.6 ml), followed by methanol (1.6 ml). When effervescence had subsided, the mixture was poured onto water (30 ml) and extracted with dichloromethane (3×30 ml). The combined organic extracts were dried over anhydrous sodium sulphate, then evaporated in vacuo to give an oil. The latter was treated with a mixture of hydrochloric acid (35%; 1.6 ml) and methanol (4 ml) and the resulting solution stirred for 18 hours. The solution was treated with water (20 ml) and aqueous sodium hydroxide (40%; 2.5 ml) then extracted with dichloromethane (3×30 ml). The combined extracts were dried over anhydrous sodium sulphate, then evaporated in vacuo to give an oil (0.42 g). Chromatography on alumina (Brockmann grade 1) with ether as eluant gave a colourless oil (0.32 g), which was dissolved in ether, and the solution washed with water (5 ×50 ml), then extracted with hydrochloric acid (0.1M; 3×30 ml). The combined aqueous extracts were extracted with dichloromethane (3×30 ml), and the combined organic extracts were dried over anhydrous sodium sulphate and evaporated in vacuo to give the title compound (E3) as a white foam (0.26 g, 61%).

Mass spectrum: Found $M^+390.1979$; $C_{21}H_{30}N_2O_3S$ requires $M^+390.1977$

EXAMPLE 4

2-(5-Chloro-2-methoxyphenyl)-5-(1-piperidinylmethyl)-1H-pyrrole (E4)

This compound was prepared by a method analogous to that used to prepare example 2, but using 2-(5-chloro-2-methoxyphenyl)-1H-pyrrole (prepared according to the method of Kruse et at., [Heterocycles, 26, 3141, 1987] from the corresponding acid chloride) in place of 2-(5-ethylsulphonyl-2-methoxyphenyl)-1H-pyrrole.

Analysis: Found C, 66.99, H, 6.94, N, 9.19%; $C_{17}H_{21}ClN_2O$ requires C, 66.60, H, 6.89, N, 8.98%.

EXAMPLE 5

2-(2,3-Dimethoxyphenyl)-5-(1-piperidinylmethyl)-1H-pyrrole (E5)

This compound was prepared by a method analogous to that used to prepare example 2, but using 2-(2,3-dimethoxyphenyl)-1H-pyrrole (prepared according to the method of Kruse et al., [Heterocycles, 26, 3141, 1987] from the corresponding acid chloride) in place of 2-(5-ethylsulphonyl-2-methoxyphenyl)-1H-pyrrole.

NMR $\delta(CDCl_3)$ 1.35–1.65 (6H, m), 2.40 (4H, m), 3.50 (2H, s), 3.80 (3H, s), 3.90 (3 H, s), 6.05 (1H, t, J=2 Hz), 6.50 (1H, t, J=2 Hz), 6.70 (1H, dd, J=9, 1 Hz), 7.00 (1H, t, J=9 Hz), 7.20 (1H, dd, J=9, 1 Hz), 9.95 (1H, br s)

EXAMPLE 6

2-(5-Ethylsulphonyl-2-methoxyphenyl)-5-[(2-(1,2,3,4-tetrahydro-isoquinolinyl))methyl]- 1H-pyrrole hydrochloride (E6)

This compound was prepared by a method analogous to that used to prepare example 1, but using 1,2,3,4-tetrahydroisoquinoline in place of piperidine, and 2-(5-ethylsulphonyl-2-methoxyphenyl)- 1H-pyrrole, in place of 2-(3,5-dibromo-2-methoxyphenyl)-1H-pyrrole.

Mass spectrum: Found $M^+410.1678$; $C_{23}H_{26}N_2O_3S$ requires $M^+410.1664$

EXAMPLE 7

2-(5-Ethylsulphonyl-2-methoxyphenyl)-5-(1-pyrrolidinylmethyl)-1H-pyrrole hydrochloride (E7)

This compound was prepared by a method analogous to that used to prepare example 1, but using pyrrolidine in place of piperidine, and 2-(5-ethylsulphonyl-2-methoxyphenyl)-1H-pyrrole in place of 2-(3,5-dibromo-2-methoxyphenyl)-1H-pyrrole.

Mass spectrum: Found $M^+348.1506$; $C_{18}H_{24}N_2O_3S$ requires $M^+348.1507$

EXAMPLE 8

2-(5-Ethylsulphonyl-2-methoxyphenyl)-5-(1-hexahydroazepinylmethyl)-1H-pyrrole hydrochloride (E8)

This compound was prepared by a method analogous to that used to prepare example 1, but using hexamethyleneimine in place of piperidine, and 2-(5-ethylsulphonyl-2-methoxyphenyl)-1H-pyrrole in place of 2-(3,5-dibromo-2-methoxyphenyl)-1H-pyrrole.

Mass spectrum: Found $M^+376.1799$; $C_{20}H_{28}N_2O_3S$ requires $M^+376.1820$

EXAMPLE 9

2-(5-Ethylsulphonyl-2-methoxyphenyl)-5-(1-(2-methylpiperidinyl)-methyl)-1H-pyrrole hydrochloride (E9)

This compound was prepared by a method analogous to that used to prepare example 1, but using 2-methylpiperidine in place of piperidine, and 2-(5-ethylsulphonyl-2-methoxyphenyl)-1H-pyrrole in place of 2-(3,5-dibromo-2-methoxyphenyl)-1H-pyrrole.

Mass spectrum: Found $M^+376.1821$; $C_{20}H_{28}N_2O_3S$ requires $M^+376.1820$

EXAMPLE 10

2-(5-Ethylsulphonyl-2-methoxyphenyl)-5-(1-(cis-2,6-dimethyl-piperidinyl)methyl)-1H-pyrrole hydrochloride (E10)

This compound was prepared by a method analogous to that used to prepare example 1, but using cis-2,6-dimethylpiperidine in place of piperidine, and 2-(5-ethylsulphonyl-2-methoxyphenyl)-1H-pyrrole in place of 2-(3,5-dibromo-2-methoxyphenyl)-1H-pyrrole.

Mass spectrum: Found $M^+390.1981$; $C_{21}H_{30}N_2O_3S$ requires $M^+390.1977$

EXAMPLE 11

2-(5-Ethylsulphonyl-2-methoxyphenyl)-5-(1-heptamethylene-iminylmethyl)-1H-pyrrole hydrochloride (E11)

This compound was prepared by a method analogous to that used to prepare example 1, but using heptamethyleneimine in place of piperidine, and 2-(5-ethylsulphonyl-2-methoxyphenyl)-1H-pyrrole in place of 2-(3,5-dibromo-2-methoxyphenyl)-1H-pyrrole.

Mass spectrum: Found $M^+390.1968$; $C_{21}H_{30}N_2O_3S$ requires $M^+390.1977$

EXAMPLE 12

2-(5-Ethylsulphonyl-2-methoxyphenyl)-5-dimethylaminomethyl-1H-pyrrole hydrochloride (E12)

This compound was prepared by a method analogous to that used to prepare example 1, but using dimethylamine in place of piperidine, and 2-(5-ethylsulphonyl-2-methoxyphenyl)-1H-pyrrole in place of 2-(3,5-dibromo-2-methoxyphenyl)-1H-pyrrole.

Mass spectrum: Found M$^+$322.1345; $C_{16}H_{22}N_2O_3S$ requires M$^+$322.1351

EXAMPLE 13

2-(5-Ethylsulphonyl-2-methoxyphenyl)-5-dipropylaminomethyl-1H-pyrrole (E13)

This compound was prepared by a method analogous to that used to prepare example 2, but using dipropylamine in place of piperidine. NMR δ(CDCl$_3$) 0.90 (6H, t, J=7 Hz), 1.25 (3H, t, J=7 Hz), 1.70 (4H, m), 2.80 (2H, m), 3.15 (2H, t, J=7 Hz), 4.05 (3H, s), 4.15 (2H, s), 6.20 (1H, t, J=2 Hz), 6.60 (1H, t, J=2 Hz), 7.05 (1H, d, J=9 Hz), 7.70 (1H, dd, J=9, 1 Hz), 8.10 (1H, d, J=1 Hz), 11.70 (1H, br s).

EXAMPLE 14

2-(5-Ethylsulfonyl-2-methoxyphenyl)-5-diethylaminomethyl-1H-pyrrole (E14)

This compound was prepared by a method analogous to that used to prepare example 2, but using diethylamine in place of piperidine.

NMR δ(CDCl$_3$) 1.10 (6H, t, J=7 Hz), 1.30 (3H, t, J=7 Hz), 2.55 (4H, q, J=7 Hz), 3.10 (2H, q, J=7 Hz), 3.65 (2H, s), 4.05 (3H, s), 6.10 (1H, t, J=2 Hz), 6.60 (1H, t, J=2 Hz), 7.05 (1H, d, J=9 Hz), 7.65 (1H, dd, J=1, 9 Hz), 8.05 (1H, d, J=1H, d, J=1 Hz), 9.75 (1 H, br s).

Mass spectrum: $^m$/z 350 (M$^+$, 20% ), 278 (100)

EXAMPLE 15

2-(1-Ethyl-2-piperidinyl)-5-(5-ethylsulphonyl-2 methoxyphenyl)-1H-pyrrole, hydrochloride (E15)

This compound was prepared by a method analogous to that used to prepare example 3 but using 1-ethylpiperidin-2-one in place of 1-ethylazepin-2-one.

Mass spectrum: Found M$^+$376.1812; $C_{20}H_{28}N_2O_3S$ requires M$^+$376.1790

EXAMPLE 16

2-(5-Ethylsulphonyl-2-methoxyphenyl)-5-[1-(1-piperidinyl)-ethyl)-1H-pyrrole hydrochloride (E16)

This compound was prepared by a method analogous to that used to prepare example 3 but using 1-acetylpiperidine in place of 1-ethylazepin-2-one.

NMR δ(CDCl$_3$) 1.27 (3H, t, J=7 Hz), 1.40 (1H,m), 1.79 (3H, d, J=7 Hz), 1.55–196 (6H,m), 2.08 (1H,m), 2.36 (1H,m), 2.46–2.80 (2H,m), 3.17 (2H, q, J=7 Hz), 3.40 (2H,m), 4.16 (3H,s), 4.53 (1H,m), 6.25 (1H,m), 6.62 (1H, m), 7.08 (1H, d, J=9 Hz), 7.70 (1H,dd, J=9, 1 Hz), 8.12 (1H, d, J=1 Hz), 11.65 (2H, br m).

EXAMPLE 17

5-(6-Chloro-benzo[b]pyran-8-yl)-2-(1-piperidinylmethyl)-1H-pyrrole hydrochloride (E17)

This compound was prepared by a method analogous to that used to prepare example 1, but using 2-(6-chloro-benzo [b]pyran-8-yl)-1H-pyrrole (prepared according to the method of Kruse et at., [Heterocycles, 26,3141, 1987] from the corresponding acid chloride) in place of 2-(3,5-dibromo-2-methoxyphenyl)-1H-pyrrole.

Mass spectrum: Found M$^+$330.1499; $C_{19}H_{23}ClN_2O$ requires M$^+$330.1499

EXAMPLE 18

2-(3-Bromo-5-ethylsulphonyl-2-methoxyphenyl)-5-(1-piperidinyl-methyl)-1H-pyrrole (E18)

This compound was prepared by a method analogous to that used to prepare example 2, but using 2-(3-bromo-5ethylsulphonyl-2-methoxy-phenyl)-1H-pyrrole (prepared according to the method of Kruse et al., [Heterocycles, 26,3141, 1987] from the corresponding acid chloride) in place of 2-(5-ethylsulphonyl-2-methoxyphenyl)-1H-pyrrole. NMR δ(CDCl$_3$) 1.30–1.70 (9H, m), 2.40 (4H, m), 3.15 (2H, q, J=7 Hz), 3.50 (2H, s), 3.80 (3H, s), 6.10 (1H, t, J=2 Hz), 6.60 (1H, t, J=2 Hz), 7.80 (1H, d, J=1 Hz), 8.00 (1H, d, J=1 Hz), 9.9 (1H, s).

EXAMPLE 19

2-(3,5-Dibromo-2-isopropoxyphenyl)-5-(1-piperidinylmethyl)-1H-pyrrole hydrochloride (E19)

This compound was prepared by a method analogous to that used to prepare example 1, but using 2-(3,5-dibromo-2-isopropoxyphenyl)-1H-pyrrole (D7) in place of 2-(3,5-dibromo-2-methoxyphenyl)-1H-pyrrole.

NMR δ(CDCl$_3$) 1.3 (6H, d, J=7 Hz), 1.6 (1H, m), 2.0 (3H, m), 2.2 (2H, m), 2.7 (2H, m), 3.6 (2H, m), 4.3 (2H, m), 4.5 (1H, septet, J=7 Hz), 6.4 (1H, m), 6.7 (1H, m) 7.7 (1H, d), 7.8 (1H, d), 11.4 (1H, brs), 12.1 (1H, br s).

Analysis: Found C, 46.25, H, 5.03, N, 5.80%; $C_{19}H_{24}N_2OBr_2 \cdot HCl$ requires C, 46.32, H, 5.11, N, 5.69%.

EXAMPLE 20

2-(3,5-Dibromo-2-isopropoxyphenyl)-5-[1-(1-piperidinyl)-ethyl]-1H-pyrrole hydrochloride hemihydrate (E20)

To 1-acetylpiperidine (0.36 ml) under argon was added phosphorous oxychloride (0.26 ml) at room temperature. The mixture was stirred at room temperature for 50 minutes and 1,2-dichloroethane (5 ml) was added. The solution was cooled to 5° C. and 2-(3,5-dibromo- 2-isopropoxyphenyl)-1H-pyrrole (D7) (0.52 g) in 1,2-dichloroethane (5 ml) was added in one portion. The mixture was stirred at 5°–10° C. for 20 minutes and was then stirred at room temperature for 22 hrs. The mixture was cooled in an ice bath and sodium borohydride (0.50 g) was added in one portion. After stirring for a further 2 hrs, water (7.2 ml) was added dropwise over 6 minutes. After a further 4 minutes, MeOH (6 ml) was added over 6 minutes. After stirring for a further 10 minutes, the mixture was partitioned between water (100 ml) and dichloromethane (50 ml). The aqueous layer was re-extracted with dichloromethane (2×40 ml) and the combined organic layers were dried over sodium sulphate. The residue was dissolved in MeOH (7 ml), dichloromethane (8 ml) and hydrochloric acid (35%; 2 ml) and was stirred at room temperature for 3 hrs. The mixture was partitioned between dichloromethane (100 ml) and water (60 ml). The aqueous layer was brought to pH 12 with 10% NaOH and was extracted with dichloromethane (2×40 ml). The combined organic layers were dried over sodium sulphate and the solvent was removed in vacuo. The residue was chromatographed on neutral alumina to give the free base of the title compound. This material was dissolved in diethyl ether (100 ml) and was washed with water and was extracted with 0.4M HCl (4×25ml). The combined HCl layers were extracted with dichloromethane (4×50 ml). The ether layer was then diluted with pentane and re-extracted with the HCl layer. The acid layer was extracted with dichloromethane and the combined dichloromethane extracts were dried over sodium sulphate and evaporated in vacuo to give the title compound (E20).

Analysis: Found C, 46.38, H, 5.63, N, 5.54%; $C_{20}H_{26}N_2OBr_2 \cdot HCl \cdot 0.5H_2O$ requires C, 46.58, H, 5.47, N, 5.43%.

EXAMPLE 21

2-(3,5-Dibromo-2-isopropoxyphenyl)-5-(N-benzyl-N-ethyl)aminomethyl-1H-pyrrole hydrochloride hemihydrate (E21)

To a solution of N-ethyl-benzylamine (0.38 ml) in EtOH (5 ml) was added formaldehyde (37–40% aqueous solution) (0.22 ml). After 10 minutes, acetic acid (0.21 ml) was added and after a further 10 minutes, 2-(3,5-dibromo-2-isopropoxyphenyl)-1H-pyrrole (D7) (0.81 g) was added in EtOH (10 ml) over 1 hr. The mixture was stirred at room temperature for two days and was then heated to 55° C. for 30 hrs. After cooling, the solvent was removed in vacuo and the residue was chromatographed on neutral alumina to give the free base. This material was dissolved in 4:1 pentane - diethyl ether and was washed with water and then extracted with 0.4M HCl. The combined HCl extracts were extracted with dichloromethane and the combined dichloromethane extracts were dried over sodium sulphate and evaporated in vacuo to give the title compound (E21).

Analysis: Found C, 50.20, H, 4.93, N, 5.13%; $C_{23}H_{25}N_2OBr_2 \cdot HCl \cdot 0.5H_2O$ requires C, 50.07, H, 5.12, N, 5.08%.

EXAMPLE 22

2-(3,5-Dibromo-2-ethoxyphenyl)-5-(1-piperidinylmethyl)-1H-pyrrole hydrochloride (E22)

Prepared analogously to Example 1, but using 2-(3,5-dibromo-2-ethoxyphenyl)-1H-pyrrole (D8) in place of 2-(3,5-dibromo-2-methoxyphenyl)-1H-pyrrole.

NMR δ(d6-DMSO) 1.3 (4H, m+t, J=6 Hz), 1.6–1.9 (5H, m), 2.8 (2H, m), 3.8 (2H, q, J=6 Hz), 4.3 (2H, m), 6.4 (1H, m), 6.8 (1H, m), 7.7 (1H, d, J=2 Hz), 7.9 (1H, d, J=2 Hz).

Analysis: Found C, 44.80, H, 4.48, N, 5.73%; $C_{18}H_{22}N_2OBr_2 \cdot HCl$ requires C, 45.17, H, 4.84, N, 5.85%.

EXAMPLE 23

2-(3,5-Dibromo-2-ethoxyphenyl)-5-[1-(1-piperidinyl)-ethyl]-1H-pyrrole hydrochloride (E23)

Prepared analogoulsy to Example 20, but using 2-(3,5-dibromo-2-ethoxyphenyl)-1H-pyrrole (D8) in place of 2-(3,5-dibromo-2-isopropoxyphenyl)-1H-pyrrole.

NMR δ(CDCl$_3$) 1.4 (4H, m+t, J=7 Hz), 1.8 (3H, d, J=7 Hz), 1.7–2.0 (3H, m), 2.15 (1H, m), 2.35 (1H, m), 2.55 (1H, m), 2.7, (1H, m), 3.4 (2H, m), 3.9 (2H, q, J=7 Hz), 4.6 (1H, m), 6.25 (1H, m), 6.7 (1H, m), 7.5 (1H, m), 7.9, (1H, m), 11.5–11.7 (2H, br s).

Analysis: Found C, 46.22, H, 4.87, N, 5.62%; $C_{19}H_{24}N_2OBr_2 \cdot HCl$ requires C, 46.32, H, 5.11, N, 5.69%.

EXAMPLE 24

2-(1-(1-Octahydroazocinyl)ethyl)-5-(3,5-dibromo-2-methoxyphenyl)-1H-pyrrole hydrochloride (E24)

Prepared by analogously to Example 2, using 1-acetyloctahydroazocine (D9) and 2-(3,5-dibromo- 2-methoxyphenyl)-1H-pyrrole (D 10).

Mass spectrum: Found M$^+$468.0412; $C_{20}H_{26}Br_2N_2O$ requires M$^+$468.0410.

EXAMPLE 25

2-(3,5-Dichloro-2-methoxyphenyl)-5-(1-piperidinylmethyl)-1H-pyrrole hydrochloride (E25)

Prepared analogously to Example 1, using 2-(3,5-dichloro-2-ethoxyphenyl)-1H-pyrrole (D11).

Mass spectrum: Found M$^+$338.0956; $C_{17}H_{20}Cl_2N_2O$ requires M$^+$338.0952.

EXAMPLE 26

2-(1-(1-Piperidinyl)ethyl)-5-(3,5-dibromo-2-methoxyphenyl)-1H-pyrrole hydrochloride (E26)

Prepared analogously to Example 2, using 1-acetylpiperidine and 2-(3,5-dibromo-2-methoxyphenyl)- 1H-pyrrole (D 10).

Mass spectrum: Found M$^+$440.0099; $C_{18}H_{22}Br_2N_2O$ requires M$^+$440.0097.

EXAMPLE 27

2-(5-Ethylsulphonyl-2-methoxyphenyl)-5-(N-benzyl-N-ethyl)-aminomethyl-1H-pyrrole hydrochloride (E27)

Prepared analogously to Example 1, using N-ethylbenzylamine and 2-(5-ethylsulphonyl-2-methoxyphenyl)- 1H-pyrrole.

Mass spectrum: Found M$^+$412.1821; $C_{23}H_{28}N_2O_3S$ requires M$^+$412.1821

EXAMPLE 28

2-(5-Bromo-2- methoxy-3- methylphenyl)-5-(1-piperidinylmethyl)-1H-pyrrole hydrochloride (E28)

Prepared analogously to Example 1, using 2-(5-bromo-3-methyl-2-methoxyphenyl)-1H-pyrrole (D13).

Mass spectrum: Found M$^+$362.0994; $C_{18}H_{23}BrN_2O$ requires 362.0993.

EXAMPLE 29

2-(3-Bromo-5-ethylsulphonyl-2-methoxyphenyl)-5-[1-(1-piperidinyl)-ethyl]-1H-pyrrole hydrochloride (E29)

Prepared analogously to Example 3 using 1-acetylpiperidine and 2-(3-bromo-5-ethylsulphonyl- 2-methoxyphenyl)-1H-pyrrole (D4).

NMR δ(CDCl$_3$) 1.3–2.8 (14H, m), 3.3–3.6 (4H, m), 3.9 (3H, s), 4.55 ( 1H, m), 6.3 (1H, m), 6.7 (1H, m), 7.9 (1H, d, J=2 Hz), 8.2 (1H, d, J=2 Hz), 11.5 ( 1H, br s), 11.9 (1H, br s).

EXAMPLE 30

2-(3-Bromo-5-ethylsulphonyl-2-methoxyphenyl)-5-(N-benzyl-N-ethyl)aminomethyl-1H-pyrrole hydrochloride (E30)

Prepared analogously to Example 21 using 2-(3-bromo-5-ethylsulphonyl-2-methoxyphenyl)-1H-pyrrole (D4).

Mass spectrum: $^m$/z 492 (M$^+$, 5%), 356 (30), 91 (100).

EXAMPLE 31

2-(2-Methoxy-5-trifluoromethylphenyl)-5-(1-piperidinylmethyl)-1H-pyrrole hydrochloride (E31)

Prepared analogously to Example 1 using 2-(2-methoxy-5-trifluoromethylphenyl)-1H-pyrrole (D17).

NMR δ(CDCl$_3$) 1.45 (1H, m), 1.8–2.3 (6H, m), 2.6 (2H, m), 3.5 (2H, m), 4.2 (5H, m), 6.3 (1H, m), 6.5 (1H, m), 7.0 (1H, d, J=8 Hz), 7.4 (1H, dd, J=8 Hz, 2 Hz), 7.8 (1H, d, J=8 Hz), 11.5 (1H, br s), 11.9 (1H, br s).

Mass spectrum: $^m$/z 338 (M$^+$, 30%), 254 (100).

EXAMPLE 32

2-(2-Methoxy-5-trifluoromethoxyphenyl)-5-(1-piperidinylmethyl)-1H-pyrrole hydrochloride hemihydrate (E32)

Prepared analogously to Example 1 using 2-(2-methoxy-5-trifluoromethoxyphenyl)-1H-pyrrole (D19).

Analysis: Found C, 54.09, H, 5.48, N, 7.07%; $C_{18}H_{21}F_3N_2O_2.HCl0.5H_2O$ requires C, 54.07, H, 5.78, N, 7.01%.

EXAMPLE 33

2-(3,5-Diiodo-2-methoxyphenyl)-5-(1-piperidinylmethyl)-1H-pyrrole hydrochloride (E33)

Prepared analogously to Example 1 using 2-(3,5-diiodo-2-methoxyphenyl)-1H-pyrrole (D20).

NMR δ($CDCl_3$) 1.3 (1H, m), 1.8–2.3 (5H, m), 2.55 (2H, m), 3.5 (2H, m), 3.7 (3H, s), 4.2 (2H, d, J=7Hz), 6.3 (1H, m), 6.6 (1H, m), 7.95 (2H, m), 11.4 (1H, br s), 11.95 (1H, br s).

EXAMPLE 34

2-(3,5-Diiodo-2-methoxyphenyl)-5-[1-(1-piperidinyl)ethyl]-1H-pyrrole hydrochloride (E34)

Prepared analogously to Example 3 but using 1-acetylpiperidine and 2-(3,5-diiodo-2-methoxyphenyl)-1H-pyrrole (D20).

Analysis: Found C, 37.98, H, 4.20, N, 4.86%; $C_{18}H_{22}I_2N_2O.HCl$ requires C, 37.75, H, 4.05, N, 4.89%.

EXAMPLE 35

2-(2,3-Dimethoxy-5-bromophenyl)-5-(1-piperidinylmethyl)-1H-pyrrole hydrochloride (E35)

Prepared analogously to Example 1 but using 2-(2,3-dimethoxy-5-bromophenyl)-1H-pyrrole (D22).

NMR δ($CDCl_3$) 1.4 (1H, m), 1.8–2.3 (6H, m), 2.6 (2H, m), 3.45 (2H, d, J=10 Hz), 3.85 (3H, s), 3.95 (3H, s), 4.2 (2H, m), 6.3 (1H, m), 6.6 (1H, m), 6.9 (1H, m), 7.4 (1H, m), 11.3 (1H, br s), 12.0 (1H, m).

Mass spectrum: $m/z$ 378 ($M^+$, 20%), 294 (100).

EXAMPLE 36

2-(2,3-Dimethoxy-5-bromophenyl)-5-[1-(1-piperidinyl)ethyl]-1H-pyrrole hydrochloride (E36)

Prepared analogously to Example 3 using 1-acetylpiperidine and 2-(2,3-dimethoxy-5-bromophenyl)-1H-pyrrole (D22).

NMR δ($CDCl_3$) 1.3 (1H, m), 1.7–2.7 (10H, m), 3.4 (2H, m), 3.85 (3H, s), 4.55 (1H, m), 6.3 (1H, m), 6.6 (1H, m), 6.9 (1H, m), 7.5 (1H, m), 11.3 (1H, br s), 11.7 (1H, m).

EXAMPLE 37

2-(2-Methoxy-5-phenylsulphonylphenyl)-5-(1-piperidinylmethyl)-1H-pyrrole oxalate hemihydrate (E37)

The free base of the title compound was prepared analogously to Example 2 using 2-(2-methoxy- 5-phenylsulphonylphenyl)-1H-pyrrole (D25). This material (0.5 g) was dissolved in ethyl acetate (10 ml) and added to a hot solution of oxalic acid (0.11 g) in ethyl acetate (10 ml). Sufficient MeOH was added to dissolve the precipitated solid and the resultant solution cooled. The resulting crystals were faltered off to give the title compound (E37).

Analysis: Found C, 59.11, H, 5.55, N, 5.64%; $C_{23}H_{26}N_2O_3S.C_2O_4.0.5H_2O$ requires C, 58.93, H, 5.74, N, 5.50%.

EXAMPLE 38

2-(2-Methoxy-5-phenylsulphonylphenyl)-5-[1-(1-piperidinyl)ethyl]-1H-pyrrole oxalate (E38)

To 1-acetylpiperidine (0.61 ml) under argon, was added phosphorus oxychloride (0.45 ml) at ambient temperature. After stirring for 0.5 h 1,2-dichloroethane (10 ml) was added and the mixture cooled to 0° C. A solution of 2-(2-methoxy-3-phenylsulphonylphenyl)-1H-pyrrole (D25) (1.0 g) in 1,2-dichloroethane (10 ml) was added dropwise over 0.3 h. Stirring was continued at 0° C. for 3 h and at ambient temperature for 18 h. The mixture was cooled to 0° C. and sodium borohydride (1 g) added portionwise over 0.16 h. Stirring was continued at ambient temperature for 2.5 h before the mixture was cooled to 0° C. Water (5 ml) followed by MeOH (5 ml) was added dropwise followed by dilution with more water (50 ml). The mixture was extracted with dichloromethane (3×200 ml) and the combined extracts dried ($Na_2SO_4$) and evaporated in vacuo. Methanol (10 ml) and concentrated HCl (4.8 ml) were added and the mixture stirred for 4 h. Water (100ml) was added and the solution basified with NaOH (10%) and extracted with dichloromethane (3×200 ml). Combined extracts were dried ($Na_2SO_4$) and evaporated in vacuo. This material was dissolved in EtOAc and added to a hot solution of oxalic acid (1 equivalent) in EtOAc. Sufficient MeOH was added to dissolve the precipitated solid and the resultant solution cooled to give the title compound (E38) (0.27 g).

NMR δ($CDCl_3$) 1.3 (1H, m), 1.7–2.05 (8H, m), 2.6 (2H, m), 3.4 (1H, m), 3.6 (1H, m), 4.0 (3H, m), 4.65 (1H, m), 6.3 (1H, m), 6.7 (1H, m), 7.0 (1H, d, J=8 Hz), 7.5 (3H, m), 7.75 (1H, d, J=8 Hz, 2 Hz), 7.95 (2H, m), 8.35 (1H, d, J=2 Hz), 11.35 (2H, br m).

EXAMPLE 39

2-(1-Benzyl-2-piperidinyl)-5-(5-ethylsulphonyl-2-methoxyphenyl)-1H-pyrrole hydrochloride (E39)

This compound was prepared by a method analogous to that used to prepare example 3, but using N-benzyl-2-piperidinone (D26) in place of 1-ethylazepin-2-one.

Mass spectrum: $m/z$ 438 ($M^+$, 100%), 381 (45), 347 (45), 173 (60) and 91 (55).

EXAMPLE 40

2-[(8-Azabicyclo[3.2.1]octan-8-yl)methyl]-5-(5-ethylsulphonyl-2-methoxyphenyl)-1H-pyrrole (E40)

Prepared analogously to Example 2, using 8-azabicyclo[3.2.1]octane hydrochloride (Chem. Abstr., 1968, 69, 35974) and carrying out the Mannich reaction at 80° C. for 3 h. The title compound (E40) was obtained as the free base.

Mass spectrum: Found $M^+$388.1825; $C_{21}H_{28}N_2O_3S$ requires 388.1820

EXAMPLE 41

2-[(3- Azabicyclo[3.2.2]nonan-3-yl)methyl]-5-(5-ethylsulphonyl-2-methoxyphenyl)-1H-pyrrole hydrochloride (E1)

Prepared analogously to Example 1, using 3-azabicyclo[3.2.2]nonane.

NMR δ($CDCl_3$) 1.25 (3H, t, J=8 Hz), 1.78 (6H, m), 2.15 (2H, m), 2.40 (2H, m), 2.75 (2H, m), 3.10 (2H, q, J=8 Hz), 3.65 (2H, m), 4.20 (3H, s), 4.25 (2H, s), 6.25 (1H, m), 6.60 (1H, m), 7.05 (1H, d, J=8 Hz), 7.70 (1H, dd, J=8 Hz, 3 Hz), 8.10 (1H, d, J=3 Hz), 10.90(1H, br s), 11.95(1H, br s).

EXAMPLE 42

2-(3,5-Dibromo-2-methoxyphenyl)-5-[1-(1-hexahydroazepinyl)-ethyl]-1H-pyrrole hydrochloride (E42)

Prepared analogously to Example 3, using 1-acetylhexahydroazepine (D27) and 2-(3,5-dibromo- 2-methoxyphenyl)-1H-pyrrole (D10).

Analysis: Found C, 46.68, H, 5.11, N, 5.68%; $C_{19}H_{24}Br_2N_2O \cdot HCl$ requires C, 46.32, H, 5.11, N, 5.69%.

EXAMPLE 43

2-[(2- Azabicyclo[2.2.2]octan-2-yl)methyl]-5-(3,5-dibromo-2-methoxyphenyl)-1H-pyrrole hydrochloride (E43)

Prepared analogously to Example 1, using 2-azabicyclo[2.2.2]octane hydrochloride [prepared by the method of Cava et al. (J. Am. Chem. Soc., 1965, 30, 3772)].

NMR δ($CDCl_3$) 1.72 (5H, m), 1.95 (1H, m), 2.03 (1H, m), 2.15 (1H, m), 2.52 (1H, m), 2.75 (1H, m), 3.25 (1H, m), 3.65 (1H, m), 3.80 (3H, s), 4.15 (1H, m), 4.35 (1H, m), 6.30 (1H, m), 6.60 (1H, m), 7.50 (1H, s), 7.80 (1H, d), 11.60 (1H, br s), 11.95 (1H, br s).

EXAMPLE 44

2-[(9-Azabicyclo[3.3.1]nonan-9-yl)methyl]-5-(3,5-dibromo-2-methoxyphenyl)- 1H-pyrrole hydrochloride (E44)

Prepared analogously to Example 1, using 9-azabicyclo[3.3.1]nonane hydrochloride (Chem. Abstr., 1968, 69, 35974). In order to effect total conversion to the desired product, the Mannich reaction was performed at room temperature for 16 h and then at 80° C. for 16 h.

Analysis: Found C, 47.60, H, 4.92, H, 5.47%. $C_{20}H_{24}Br_2N_2O \cdot HCl$ requires C, 47.60, H, 4.99, N, 5.55%.

EXAMPLE 45

2-(3,5-Dibromo-2-methoxyphenyl)-5-[1-(1-piperidinyl)propyl]-1H-pyrrole hydrochloride (E45)

Prepared analogously to Example 3, using 1-propionylpiperidine (D28) and 2-(3,5-dibromo- 2-methoxyphenyl)-1H-pyrrole (D10).

Analysis: Found C, 46.70, H, 5.22, N, 5.63%. $C_{19}H_{24}N_2OBr_2 \cdot HCl$ requires C, 46.32, H, 5.11, N, 5.69%.

EXAMPLE 46

2-(N-Cyclohexylmethyl-N-ethylaminomethyl)-5-(3,5-dibromo-2-methoxyphenyl)-1H-pyrrole oxalate (E46)

To a mixture of 5-(3,5-Dibromo-2-methoxyphenyl)-1H-pyrrole-2-carboxaldehyde (D29) (0.31 g, 0.9 mmol), N-ethylcyclohexanemethylamine (D31) (0.12 g, 0.9 mmol) and triethylamine (0.35 ml, 2.6 mmol) in dry dichloromethane (15 ml) under argon was added dropwise a solution of titanium tetrachloride in dichloromethane (1M; 0.45 ml) at room temperature with constant stirring. The reaction mixture was stirred for 18 h, and was then quenched with a solution of sodium cyanoborohydride (0.16 g, 2.5 mmol) in dry methanol (6 ml). The resulting solution was stirred at room temperature for 18 h and was then basified to pH 13 with aqueous 5N sodium hydroxide. The organic layer was separated and the aqueous layer was extracted with ethyl acetate. The combined organic extracts were dried ($Na_2SO_4$) and evaporated in vacuo to give a brown off. Chromatography on alumina (Brockmann grade 1) with pentane - ethyl acetate (10–100%) gradient elution gave the free base of the title compound (0.19 g). The free base was dissolved in hot ethyl acetate (20 ml) and treated with a solution of oxalic acid (0.035 g) in ethyl acetate. On cooling the mixture, the title compound (E46) was obtained as a pink solid (0.025 g).

NMR δ($CDCl_3$) 0.90 (2H, m), 1.18 (4H, m), 1.35 (3H, t, J=7 Hz), 1.70 (5H, m), 2.85 (2H, m), 3.18 (2H, m), 3.75 (3H,s), 4.20 (3H, m), 6.30 (1H, m), 6.63 (1H, m), 7.55 (1H, s), 7.70 (1H, s), 11.40 (1H, br s), 11.30 (1H, br s).

EXAMPLE 47

2-[2-Phenyl-1-(1-piperidinyl)ethyl]-5-(5-bromo-2,3-dimethoxyphenyl)-1H-pyrrole (E47)

Prepared analogously to Example 3, using 1-phenylacetylpiperidine (D32) and 2-(2,3-dimethoxy- 5-bromophenyl)-1H-pyrrole (D22). The title compound (E47) was obtained as the free base.

Analysis: Found C, 63.84, H, 6.20, N, 6.09. $C_{25}H_{29}BrN_2O_2$ requires C, 63.97, H, 6.23, N, 5.97.

EXAMPLE 48

2-(5-Ethylsulphonyl-2-methoxyphenyl)-5-[1-(1-piperidinyl)-ethyl]-1H-pyrrole, faster eluting enantiomer (E48)

The free base was obtained from 2-(5-Ethylsulphonyl-2-methoxyphenyl)-5-[1-(1-piperidinyl)-ethyl]-1H-pyrrole hydrochloride (E16) by partition between aqueous sodium bicarbonate and dichloromethane. The resulting material (55.92 mg) was injected, in 2.16 mg aliquots onto a CHIRALCEL OJ column (250×20 mm), and isocratic elution was carried out with hexane followed by hexane—ethanol (80:20) at a rate of 10.0 ml min$^{-1}$. The faster eluting material was obtained from each run, and evaporation of the combined relevant fractions gave the title compound (E48) (23.4 mg). HPLC analysis: enantiomeric purity >97.5%

EXAMPLE 49

2-(5-Ethylsulphonyl-2-methoxyphenyl)-5-[1-(1-piperidinyl)-ethyl]-1H-pyrrole, slower eluting enantiomer (E49)

From the chromatography described in example 48, the slower eluting material was obtained from each run, and evaporation of the combined relevant fractions gave the title compound (E48) (13.4 mg).

HPLC analysis: enantiomeric purity >96%

EXAMPLE 50

2-(5-Ethylsulfonyl-2- methoxyphenyl)-5-(1-(1,2,3,6-tetrahydro-pyridinyl)methyl)-1H-pyrrole hydrochloride (E50)

This compound was prepared by a method analogous to that used to prepare example 1, but using 1,2,3,6-tetrahydropyridine in place of piperidine, and 2-(5-ethylsulphonyl-2-methoxyphenyl)-1H-pyrrole in place of 2-(3,5-dibromo-2-methoxyphenyl)-1H-pyrrole.

Mass spectrum: Found M$^+$360.1496; $C_{19}H_{24}N_2O_3S$ requires M$^+$360.1508.

EXAMPLE 51

2-(5-Ethylsulfonyl-2-methoxyphenyl)-5-(1-(1-(1,2,3,6-tetrahydropyridinyl))ethyl)-1H-pyrrole hydrochloride (E51)

This compound was prepared by a method analogous to that used to prepare example 3, but using 1-acetyl-1,2,3,6-tetrahydropyridine (D33) in place of 1-ethylazepin-2-one.

NMR δ($CDCl_3$) 1.27 (3H, t, J=7 Hz), 1.81, 1.90 (3H, 2×d, J=6 Hz), 2.33 (1H, br m), 2.75–3.75 (6H, br m), 3.16 (2H, q, J=7 Hz), 4.17 (3H, s), 4.56, 4.73 (1H, 2×br m), 5.56 (1H, m), 5.98 (1H, m), 6.28 (1H, m), 6.62 (1H, m), 7.09 (1H, d, J=10 Hz), 7.72 (1H, dd, J=10, 2 Hz),8.13 (1H, d,J=2 Hz), 11.49, 11.63 (1H, 2×br s),12.21, 12.34 (1H, 2×br s).

EXAMPLE 52

2-[(2-Azabicyclo[3.2.1]octan-2-yl)methyl]-5-(5-ethylsulphonyl-2-methoxyphenyl)-1H-pyrrole hydrochloride (E52)

This compound was prepared by a method analogous to that used to prepare example 1, but using 2-azabicyclo[3.2.1]octane [prepared by the method of Barraclough et al., (*Tetrahedron*, 1979, 35, 91)] in place of piperidine, and 2-(5-ethylsulphonyl-2-methoxyphenyl)-1H-pyrrole in place of 2-(3,5-dibromo-2-methoxyphenyl)-1H-pyrrole.

NMR δ(CDCl$_3$) 1.30 (3H, t, J=8 Hz), 1.65 (4H, m), 1.92 (3H, m), 2.42 (1H, m), 2.52 (1H, m), 2.66 (1H, m), 3.15 (2H, q, J=7 Hz), 3.29 (1H, m), 3.70 (1H, m), 4.00 (1H, m), 4.13 (1H, m), 4.21 (3H, s), 6.24 (1H, m), 6.62 (1H, m), 7.10 (1H, d, J=2 Hz), 7.70(1H, dd, J=9 Hz and 2 Hz), 8.11 (1H, d, J=9 Hz), 11.60 (1H, br s) and 11.92 (1H, br s).

EXAMPLE 53

2-(5-Ethylsulphonyl-2-methoxyphenyl)-5-[1-(1-pyrrolidinyl)-ethyl]-1H-pyrrole (E53)

This compound was prepared by a method analogous to that used to prepare example 3, but using N-acetyl-2-pyrrolidinone (D34) in place of 1-ethylazepin-2-one.

Mass spectrum: $^m$/z 363 (MH$^+$, 7.5%), 143 (55) and 72 (100).

EXAMPLE 54

2-(5-Ethylsulphonyl-2-methoxyphenyl)-5-[N-ethyl-N-(2-thienyl)methylaminomethyl]-1H-pyrrole hydrochloride (E54)

This compound was prepared by a method analogous to that used to prepare example 1, but using N-ethyl-N-(2-thienyl)methylamine in place of piperidine, and 2-(5-ethylsulphonyl-2-methoxyphenyl)- 1H-pyrrole in place of 2-(3, 5-dibromo-2-methoxyphenyl)-1H-pyrrole.

NMR δ(CDCl$_3$) 1.28 (3H, t, J=7 Hz), 1.46 (3H, t, J=7 Hz), 2.95 ( 1H, m), 3.05 (1H, m), 3.14 (2H, q, J=7 Hz), 4.21 (3H, s), 4.25 (3H, m), 4.50 (1H, m), 6.34 (1H, t, J=6 Hz), 6.64 (1H, t, J=6 Hz), 7.10 (1H, d, J=9 Hz), 7.13 (1H, dd, J=5 Hz and 4 Hz), 7.36 (1H, d), 7.47 (1H, dd, J=5 Hz and 1 Hz), 7.71 (1H, dd, J=9 Hz and 2 Hz), 8.12 (1H, d, J=2 Hz), 11.70 (1H, br. s) and 12.60 (1H, br. s).

EXAMPLE 55

2-(5-Ethylsulphonyl-2-methoxyphenyl)-5-[N -ethyl-N-(2-furyl)methyl-aminomethyl]-1H-pyrrole hydrochloride (E55)

This compound was prepared by a method analogous to that used to prepare example 1, but using N-ethyl-N-(2-furyl)methylamine in place of piperidine, and 2-(5-ethylsulphonyl-2-methoxyphenyl)-1H-pyrrole in place of 2-(3,5-dibromo-2-methoxyphenyl)-1H-pyrrole.

Mass spectrum: m/z 403 (M$^+$, 35%), 278 (15) and 126 (100).

EXAMPLE 56

2-(5-Ethylsulphonyl-2-methoxyphenyl)-5-(N-benzyl-N-propyl-aminomethyl)-1H-pyrrole hydrochloride (E56)

This compound was prepared by a method analogous to that used to prepare example 1, but using N-propylbenzylamine in place of piperidine, and 2-(5-ethylsulphonyl-2-methoxyphenyl)-1H-pyrrole in place of 2-(3,5-dibromo-2-methoxyphenyl)-1H-pyrrole.

NMR δ(CDCl$_3$) 0.84 (3H, t, J=7 Hz), 1.28 (3H, t, J=7 Hz), 1.79 (2H, m), 2.78 (2H, m), 3.14 (2H, q, J=7 Hz), 3.92 (1H, m), 4.18 (1H, m), 4.21 (3H, s), 4.40 (2H, m), 6.29 (1H, t, J=3 Hz), 6.62 (1H, t, J=3 Hz), 7.10 (1H, d, J=9 Hz), 7.45 (3H, m), 7.61 (2H, m), 7.71 (1H, dd, J=9 Hz and 2 Hz), 8.12 (1H, d, J=2 Hz), 11.82 (1H, br. s) and 12.23 (1H, br. s).

EXAMPLE 57

2- (3-Bromo-5-ethylsulphonyl-2-methoxyphenyl)-5-[N-ethyl-N-( 4-methoxyphenyl)methyl-aminomethyl]-1H-pyrrole hydrochloride (E57)

This compound was prepared by a method analogous to that used to prepare example 48, but using 5-(3-bromo-5-ethylsulphonyl-2-methoxyphenyl)-1H-pyrrole-2-carboxaldehyde (D36) in place of 5-(3,5-dibromo-2-methoxyphenyl)-1H-pyrrole-2-carboxaldehyde, and N-ethyl-N-(4-methoxy)benzylamine in place of 1-ethylcyclohexanemethylamine.

Mass spectrum: m/z 522 (M$^+$, 7%), 356 (10), 164 (25) and 121 (100).

EXAMPLE 58

2-(5-Ethylsulphonyl-2-methoxyphenyl)-5-[N-ethyl-N-(4-methoxyphenyl)methylaminomethyl]-1H-pyrrole hydrochloride (E58)

This compound was prepared by a method analogous to that used to prepare example 1, but using N-ethyl-N-(4-methoxy)benzylamine in place of piperidine, and 2-(5-ethylsulphonyl-2-methoxyphenyl)- 1H-pyrrole in place of 2-(3, 5-dibromo-2-methoxyphenyl)-1-H-pyrrole.

Mass spectrum: Found M$^+$442.1920; C$_{24}$H$_{30}$N$_2$O$_4$S requires 442.1926.

EXAMPLE 59

2-(5-Dimethylsulphamoyl-2-methoxyphenyl)-5-[1-(piperidinyl)]methyl-1H-pyrrole (E59)

a) 5-N,N-Dimethylsulphamoyl-2-methoxybenzoic acid (6.89 g, 2.7 mmol) in anhydrous methylene chloride (50 ml) was treated with oxalyl chloride (5.0 ml) and anhydrous dimethylformamide (2–3 drops) at room temperature for one hour. The resulting solution was evaporated to dryness and azeotroped with anhydrous toluene (2×50 ml). Trituration of the residue gave the acid chloride (6.4 g; 87%) as colourless microcrystals.

b) 2-(2-Bromoethyl)-1,3-dioxolane (5.3 g, 3.43 ml, 2.9 mmol) was added dropwise to dry magnesium (0.8 g, 3.5 mmol; 1.3 equivalents) in THF at 25° C. under argon. The temperature was maintained between 25° C. and 29° C. during addition. The solution was left to stir for one hour at 25° C. The grignard solution was added to anhydrous cuprous bromide (7.6 g, 2.66 mmol) at 0°–3° C. in THF (10 ml) over 20 minutes. The very dark red mix was stirred at 0° C. for 45 minutes then cooled to −75° C. Dried acid chloride (6.4 g, 2.3 mmol, from pan (a)) in THF (50 ml) was added dropwise at −70° C. over 30 minutes and the final mix stirred for one hour at −70° C. before being allowed to reach ambient temperatures over a period of 40 minutes and stir for a further hour. The mix was poured into a mix of 10% aqueous citric acid (200 ml) and ethyl acetate (200 ml) and stirred for 15 minutes. The mix was allowed to settle and the organic layer separated. The aqueous organic mix was filtered through kieselguhr and extracted with ethyl acetate (3×150 ml). The combined organic extracts were dried over anhydrous sodium sulphate, filtered and evaporated in vacuo. This was taken up in methylene chloride and filtered.

Evaporation in vacuo gave an oil which was chromatographed on Kieselgel 7734 with 1–20 ethyl acetate in methylene chloride to give 2-[2-(5-N,N-dimethylsulphamoyl-2-methoxybenzoyl)ethyl]-1,3-dioxolane (5.17 g; 66%) as colourless microcrystals, mp 114°–115° C. (Found: C,52.15,52.09;H,5.99,5.96; N,4.05,4.01 ;$C_{15}H_{21}NO_6S$ requires C,52.17 ;H,6.16;N,4.08)

c) The dioxolane(5.0 g, 14.5 mmol, product of pan (b)) was dissolved in THF (10 ml) and treated with 2N hydrochloric acid (10 ml) at reflux for 2 hrs under argon. The mix was diluted with cold water (50 ml) and ethyl acetate (50 ml). The organic layer was separated and the aqueous layer further extracted with ethyl acetate (2×50 ml). The combined organic extracts were washed with water (30 ml), brine (30 ml) and dried over sodium sulphate. Filtration, evaporation and retreatment as above gave the 3-(5-N,N-dimethylsulphamoyl- 2-methoxybenzoyl)propanol (3.5 g; 81%) which was used without further purification. This propanal (3.5 g, 1.17 mmol) was heated in ethanol (20 ml) containing ammonium acetate (4.5 g) for 2–3 hrs. The mix was evaporated in vacuo to one quarter volume then partitioned between water (50 ml) and ethyl acetate (80 ml). The organic layer was separated and the aqueous layer further extracted with ethyl acetate (2×50 ml). The combined organic extracts were washed with water (30 ml), brine (30 ml) and dried over anhydrous sodium sulphate. Filtration, and evaporation in vacuo gave an oil which slowly crystallised. Chromatography on Kieselgel 7734 gave 2-(5-NN-dimethylsulphamoyl-2-methoxyphenyl)- 1H-pyrrole (2.1 g; 64 %) as off-white microcrystals, mp 129°–130° C. (Found C,55.38,55.73;H,5.62,5.73;N,9.71,9.87; $C_{13}H_{16}N_2O_3S$ requires C,55.70;H,5.75;N,9.99).

d) Piperidine (0.11 ml) was added to ethanol (3 ml) containing formaldehyde (0.01 ml) and stirred for 30 min. Glacial acetic acid (0.06 ml) was added and the mix stirred for a further 10 min. The pyrrole (0.28 g, 1 mmol) was added and the mix stirred at room temperature for several days. The mix was evaporated to a low volume and partitioned between methylene chloride (50 ml), saturated aqueous potassium carbonate (30 ml) and water (30 ml). The organic layer was separated and the aqueous layer further extracted with methylene chloride (2×50 ml). The combined organic extracts were washed with water and dried over sodium sulphate. Filtration and evaporation in vacuo gave a crude solid which was chromatographed on Kieselgel 7734 via 1–4 % methanol in methylene chloride to give the title compound (0.102 g; 27 %) as off-white microcrystals mp 78°–79° C.

Mass spectrum: Found M+, 377.175690; $C_{19}H_{27}N_3O_3S$ Calc. 377.177314.

Analysis Found C,57.51.57.38;N,10.75,10.77 $C_{19}H_{27}N_3O_3S.1H_2O$ requires C,57.72;H,7.34;N,10.63).

$^1$H NMR (CDCl$_3$) δ:1.45–1–8 (6H, br m), 2.48–2.62 (4H, br m), 2.71 (6H, s), 3.65 (2H, s), 4.09 (3H, s), 6.12 (1H, br m), 6.6 (1H, br m), 7.0 (1H, d, J=9 Hz), 7.54 (1H, dd, J=9,2 Hz), 7.99 (1H, d, J=2 Hz).

EXAMPLE 60

The following compounds were prepared by methods analogous to those used to prepare the examples described hereinbefore.

2-[(2-Azabicyclo[2.2.1]heptan-2-yl)methyl]-5-(5-ethylsulphonyl-2-methoxyphenyl)- 1H-pyrrole hydrochloride.

2-[(2-Azabicyclo[2.2.1]hept-5-en-2-yl)methyl]-5-(5-ethylsulphonyl- 2-methoxyphenyl)-1H-pyrrole hydrochloride.

2-[(2- Azabicyclo[3.2.1]oct-6-en-2-yl)methyl]-5-(5-ethylsulphonyl- 2-methoxyphenyl)-1H-pyrrole hydrochloride.

2-(2-Methoxy-5-methylsulphonylphenyl)-5-(1-piperidinylmethyl)-1H-pyrrole hydrochloride.

2-(2,3-Dimethoxy-5-ethylsulphonylphenyl)-5-(1 -piperidinylmethyl)-1H-pyrrole hydrochloride.

2-[(3- Azabicyclo[3.2.1]octan-3-yl)methyl]-5-(5-ethylsulphonyl-2-methoxyphenyl)-1H-pyrrole hydrochloride.

2-(5-Ethylsulphonyl-2-methoxyphenyl)-5-[N-ethyl-N-[1-( 1,2,3,4-tetrahydro)naphthyl]-aminomethyl]-1H-pyrrole hydrochloride.

2-(2-Ethyl-2-azabicyclo[2.2.1]heptan-3-yl)-5-(5-ethylsulphonyl-2-methoxyphenyl)- 1H-pyrrole hydrochloride.

2-[1-(2-Azabicyclo[2.2.1]heptan-2-yl)ethyl]-5-(5-ethylsulphonyl-2-methoxyphenyl)-1H-pyrrole hydrochloride.

2-(5-Ethylsulphonyl-2-methoxyphenyl)-5-[N-ethyl-N-(1-naphthyl)methyl-aminomethyl]-1H-pyrrole hydrochloride.

2-(5-Isopropylsulphonyl-2-methoxyphenyl)-5-(1-piperidinylmethyl)-1H-pyrrole hydrochloride.

(±)Trans-2-(5-ethylsulphonyl-2-methoxyphenyl)-5-(perhydroisoquinolinylmethyl)-1H-pyrrole hydrochloride.

DATA

The ability of the compounds to bind selectively to human $D_3$ dopamine receptors can be demonstrated by measuring their binding to cloned receptors. The inhibition constants ($K_i$) of test compounds for displacement of [$^{125}$I] iodosulpride binding to human $D_2$ and $D_3$ dopamine receptors expressed in CHO cells have been determined. The cell lines were shown to be free from bacterial, fungal and mycoplasmal contaminants, and stocks of each were stored frozen in liquid nitrogen. Cultures were grown as monolayers or in suspension in standard cell culture media. Cells were recovered by scraping (from monolayers) or by centrifugation (from suspension cultures), and were washed two or three times by suspension in phosphate buffered saline followed by collection by centrifugation. Cell pellets were stored frozen at −40° C. Crude cell membranes were prepared by homogenisation followed by high-speed centrifugation, and characterisation of cloned receptors achieved by radioligand binding.

Preparation of CHO cell membranes

Cell pellets were gently thawed at room temperature, and resuspended in about 20 volumes of ice-cold 50 mM Tris salts (pH 7.4 @37° C.), 20 mM EDTA, 0.2M sucrose. The suspension was homogenised using an Ultra-Turrax at full speed for 15 sec. The homogenate was centrifuged at 18,000 r.p.m for 20 min at 4° C. in a Sorvall RC5C centrifuge. The membrane pellet was resuspended in ice-cold 50 mM Tris salts (pH 7.4 @37° C.), using an Ultra-Turrax, and recentrifuged at 18,000 r.p.m for 15 min at 4° C. in a Sorvall RC5C. The membranes were washed two more times with ice-cold 50 mM Tris salts (pH 7.4 @37° C.). The final pellet was resuspended in 50 mM Tris salts (pH 7.4 @37° C.), and the protein content determined using bovine serum albumin as a standard (Bradford, M. M. (1976) Anal. Biochem. 72, 248–254).

Binding experiments on cloned dopamine receptors

Crude cell membranes were incubated with 0.1 nM [$^{125}$I] iodosulpride (~2000 Ci/mmol; Amersham, U.K.), and the test compound in a buffer containing 50 mM Tris salts (pH 7.4 @37° C.), 120 mM NaCl, 5 mM KCl, 2 mM $CaCl_2$, 1 mM $MgCl_2$, 0.1% (w/v) bovine serum albumin, in a total volume of 1 ml for 30 min at 37° C. Following incubation, samples were filtered using a Brandel Cell Harvester, and washed three times with ice-cold 50 mM Tris salts (pH 7.4 @37° C.), 120 mM NaCl5 mM KCl2 mM $CaCl_{2,}$ 1 mM MgCl$_2$. The radioactivity on the filters was measured using a Cobra gamma counter (Canberra Packard). Non-specific binding was defined as the radioligand binding remaining after incubation in the presence of 100 μM iodosulpride. For competition curves, 14 concentrations (half-log dilutions) of competing cold drug were used.

Competition curves were analysed simultaneously whenever possible using non-linear least-squares fitting procedures, capable of fitting one, two or three site models.

Results

The compounds of Examples 1, 2, 16, 27, 30, 36 and 49 had IC$_{50}$ values in the range 0.2–26 nM at the human D$_3$ receptor.

Pharmaceutical Formulations

The following represent typical pharmaceutical formulations according to the present invention, which may be prepared using standard methods.

| IV Infusion | |
|---|---|
| Compound of formula (I) | 1–40 mg |
| Buffer | to pH ca 7 |
| Sovent/complexing agent | to 100 ml |
| Bolus Injection | |
| Compound of formula (I) | 1–40 mg |
| Buffer | to pH ca 7 |
| Co-Solvent | to 5 ml |
| Buffer: | Suitable buffers include citrate, phosphate, sodium hydroxide/hydrochloric acid. |
| Solvent: | Typically water but may also include cyclodextrins (1–100 mg) and co-solvents such as propylene glycol, polyethylene glycol and alcohol. |
| Tablet | |
| Compound | 1–40 mg |
| Diluent/Filler* | 50–250 mg |
| Binder | 5–25 mg |
| Disentegrant | 5–50 mg |
| Lubricant | 1–5 mg |
| Cyclodextrin | 1–100 mg |
| *may also include cyclodextrim | |
| Diluent: | e.g. Microcrystalline cellulose, lactose, starch |
| Binder: | e.g. Polyvinylpyrrolidone, hydroxypropymethyl-cellulose |
| Disintegrant: | e.g. Sodium starch glycollate, crospovidone |
| Lubricant: | e.g. Magnesium stearate, sodium stearyl fumarate. |
| Oral Suspension | |
| Compound | 1–40 mg |
| Suspending Agent | 0.1–10 mg |
| Diluent | 20–60 mg |
| Preservative | 0.01–1.0 mg |
| Buffer | to pH ca 5–8 |
| Co-solvent | 0–40 mg |
| Flavour | 0.01–1.0 mg |
| Colourant | 0.001–0.1 mg |
| Suspending agent: | e.g. Xanthan gum, microcyrstralline cellulose |
| Diluent: | e.g. sorbitol solution, typically water |
| Preservative: | e.g. sodium benzoate |
| Buffer: | e.g. citrate |
| Co-solvent: | e.g. alcohol, propylene glycol, polyethylene glycol, cyclodextrin |

We claim:

1. A compound of formula (I):

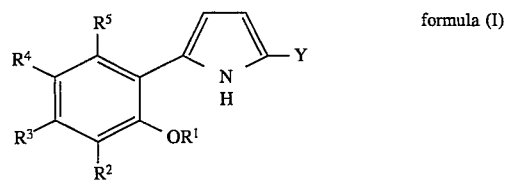

formula (I)

wherein

R$^1$ represents C$_{1-4}$alkyl; and

R$^2$, R$^3$, R$^4$ and R$^5$ each independently represent hydrogen, halogen, C$_{1-4}$alkyl, C$_{1-4}$alkoxy, C$_{1-4}$alkoxyC$_{1-4}$alkyl, C$_{1-4}$alkylsulphonyl, trifluoromethylsulphonyl; optionally substituted arylsulphonyl, optionally substituted heteroarylsulphonyl, optionally substituted aralkylsulphonyl, optionally substituted heteroaralkylsulphonyl, nitro, cyano, amino, mono- or di-alkylamino, trifluoromethyl, trifluoromethoxy, hydroxyl, hydroxyalkyl, C$_{1-4}$alkylthio, C$_{1-4}$alkanoyl, C$_{1-4}$alkoxycarbonyl, aminosulphonyl, alkylaminosulphonyl or dialkylaminosulphonyl; or R$^1$ and R$^2$ together form a linking chain —(CH$_2$)$_m$Op; (wherein m is 2 to 4 and p is zero or 1) which chain may be optionally substituted by one or two C$_{1-4}$alkyl groups; and Y represents a group selected from:

(a)

or

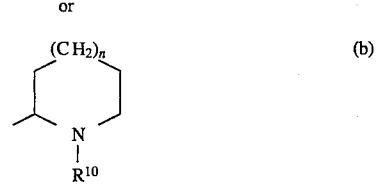

(b)

wherein

R$^6$ and R 7 independently represent hydrogen, C$_{1-6}$alkyl, optionally substituted arylC$_{1-6}$alkyl or optionally substituted heteroarylC$_{1-6}$alkyl;

R$^8$ represents C$_{1-6}$alkyl, C$_{3-6}$alkenyl or C$_{3-6}$cycloalkyl C$_{1-4}$alkyl; and R$^9$ represents C$_{1-6}$alkyl; C$_{3-6}$alkenyl; C$_{3-6}$cycloalkyl C$_{1-4}$alkyl, optionally substituted arylC$_{1-4}$alkyl or optionally substituted heteroaryl C$_{1-4}$alkyl;

or

NR$^8$R$^9$ forms a heterocyclic ring which has from 4 to 10 ring members, is fully or partially saturated and is optionally substituted by one or more C$_1$ to C$_4$ alkyl groups or fused to an aromatic ring: said heterocyclic ring optionally containing a sulphur atom, provided there are at least two methylene groups between the S and N atoms and said heterocyclic ring further optionally containing a C$_1$–C$_3$ alkylene bridge (with the proviso that NR$^8$R$^9$ is not piperazine);

R$^{10}$ represents C$_{1-6}$alkyl; C$_{3-6}$alkenyl; C$_{3-6}$cycloalkylC$_{1-4}$alkyl, optionally substituted arylC$_{1-4}$alkyl or optionally substituted heteroarylC$_{1-4}$alkyl; and n is 1 to 3; or a pharmaceutically acceptable salt thereof.

2. A compound according to claim 1 wherein R$^1$ represents methyl, ethyl, or isopropyl.

3. A compound according to claim 1 wherein at least one of R$^2$ to R$^5$ is hydrogen, and the other substituents are selected from halogen, C$_{1-2}$alkyl, C$_{1-2}$alkoxy, C$_{1-2}$alkylsulphonyl, phenylsulphonyl, CF$_3$, CF$_3$O and dialkylaminosulphonyl.

4. A compound according to claim 1 wherein Y represents a group (a) in which R$^6$ represents hydrogen, and R$^7$ represents hydrogen or methyl.

5. A compound according to claim 1 wherein Y represents a group (a) in which R$^8$ represents C$_{1-4}$alkyl and R$^9$ represents C$_{1-4}$alkyl, cyclopropylmethyl, allyl or optionally substituted phenylmethyl; or -NR$^8$R$^9$ forms a fully or partially saturated 5 to 8 membered heterocyclic ring, optionally including a C$_{1-3}$alkylene bridge.

6. A compound according to claim 1 wherein Y represents a group (b) in which $R^{10}$ represents $C_{1-4}$alkyl, cyclopropylmethyl, allyl or benzyl.

7. A compound according to claim 1 selected from:

2-(3,5-dibromo-2-methoxyphenyl)-5-(1-piperidinylmethyl)-1H-pyrrole, 2-(5-ethylsulphonyl-2-methoxyphenyl)-5-(1-piperidinylmethyl)-1H-pyrrole, 2-(1-ethyl-2-hexahydroazepinyl)-5-(5-ethylsulphonyl-2methoxyphenyl)-1H-pyrrole, 2-(5-chloro-2-methoxyphenyl)-5-(1-piperidinylmethyl)-1H-pyrrole, 2-(2,3-dimethoxyphenyl)-5-(1-piperidinylmethyl)-1H-pyrrole, 2-(5-ethylsulphonyl-2-methoxyphenyl)-5-[(2-(1,2,3,4-tetrahydro-isoquinolinyl))methyl]- 1H-pyrrole, 2-(5-ethylsulphonyl-2-methoxyphenyl)-5-(1-pyrrolidinylmethyl)-1H-pyrrole, 2-(5-ethylsulphonyl-2-methoxyphenyl)-5-(1 -hexahydroazepinylmethyl)-1H-pyrrole, 2-(5-ethylsulphonyl-2-methoxyphenyl)-5-(1-(2-methylpiperidinyl)-methyl)-1H-pyrrole, 2-(5-ethylsulphonyl-2-methoxyphenyl)-5-(1-(cis-2,6-dimethyl-piperidinyl)methyl)-1H-pyrrole, 2-(5-ethylsulphonyl-2-methoxyphenyl)-5-(1-heptamethylene-iminylmethyl)-1H-pyrrole, 2-(5-ethylsulphonyl-2-methoxyphenyl)-5-dimethylaminomethyl-1H-pyrrole, 2-(5-ethylsulphonyl-2-methoxyphenyl)-5-dipropylaminomethyl-1H-pyrrole, 2-(5-ethylsulphonyl-2-methoxyphenyl)-5-diethylaminomethyl-1H-pyrrole, 2-(1-ethyl-2-piperidinyl)-5-(5-ethylsulphonyl-2 methoxyphenyl)-1H-pyrrole, 2-(5-ethylsulphonyl-2-methoxyphenyl)-5-[1-(1-piperidinyl)-ethyl]-1H-pyrrole, 5-(6-chloro-benzo[b]pyran-8-yl)-2-(1-piperidinylmethyl)-1H-pyrrole, 2-(3-bromo-5-ethylsulphonyl-2-methoxyphenyl)-5-(1-piperidinyl-methyl)-1H-pyrrole, 2-(3,5-dibromo-2-isopropoxyphenyl)-5-(1 -piperidinylmethyl)-1H-pyrrole, 2-(3,5-dibromo-2-isopropoxyphenyl)-5-[1-(1-piperidinyl)-ethyl]-1H-pyrrole, 2-(3,5-dibromo-2-isopropoxyphenyl)-5-(N-benzyl-N-ethyl)aminomethyl-1H-pyrrole, 2-(3,5-dibromo-2-ethoxyphenyl)-5-(1 -piperidinylmethyl)-1H-pyrrole, 2-(3,5-dibromo-2-ethoxyphenyl)-5-[1-(1-piperidinyl)-ethyl]-1H-pyrrole, 2-(1-(1-octahydroazocinyl)ethyl)-5-(3,5-dibromo-2-methoxyphenyl)-1H-pyrrole, 2-(3,5-dichloro-2-methoxyphenyl)-5-(1-piperidinylmethyl)-1H-pyrrole, 2-(1-(1-piperidinyl)ethyl)-5-(3,5-dibromo-2-methoxyphenyl)-1H-pyrrole, 2-(5-ethylsulphonyl-2-methoxyphenyl)-5-(N-benzyl-N-ethyl)-aminomethyl-1H-pyrrole, 2-(5-bromo-2-methoxy-3-methylphenyl)-5-(1-piperidinylmethyl)-1H-pyrrole, 2-(3-bromo-5-ethylsulphonyl-2-methoxyphenyl)-5-[1-(1-piperidinyl)-ethyl]-1H-pyrrole, 2-(3-bromo-5-ethylsulphonyl-2-methoxyphenyl)-5-(N-benzyl-N-ethyl)aminomethyl-1H-pyrrole, 2-(2-methoxy-5-trifluoromethylphenyl)-5-(1-piperidinylmethyl)-1H-pyrrole, 2-(2-methoxy-5-trifluoromethoxyphenyl)-5-(1-piperidinylmethyl)-1H-pyrrole, 2-(3,5-diiodo-2-methoxyphenyl)-5-(1-piperidinylmethyl)-1H-pyrrole, 2-(3,5-diiodo-2-methoxyphenyl)-5-[1-(1-piperidinyl)ethyl]-1H-pyrrole, 2-(2,3-dimethoxy-5-bromophenyl)-5-(1 -piperidinylmethyl)-1H-pyrrole, 2-(2,3-dimethoxy-5-bromophenyl)-5-[1-(1-piperidinyl)ethyl]-1H-pyrrole, 2-(2-methoxy-5-phenylsulphonylphenyl)-5-(1 -piperidinylmethyl)-1H-pyrrole, 2-(2-methoxy-5-phenylsulphonylphenyl)-5-[1-(1-piperidinyl)ethyl]-1H-pyrrole, 2-(1-benzyl-2-piperidinyl)-5-(5-ethylsulphonyl-2-methoxyphenyl)-1H-pyrrole, 2-[(8-azabicyclo[3.2.1]octan-8-yl)methyl]-5-(5-ethylsulphonyl-2-methoxyphenyl)- 1H-pyrrole, 2-[(3-azabicyclo[3.2.2]nonan-3-yl)methyl]-5-(5-ethylsulphonyl-2-methoxyphenyl)- 1H-pyrrole, 2-(3,5-dibromo-2-methoxyphenyl)-5-[1-(1-hexahydroazepinyl)-ethyl]-1H-pyrrole, 2-[(2-azabicyclo[2.2.2]octan-2-yl)methyl]-5-(3,5-dibromo-2-methoxyphenyl)- 1H-pyrrole, 2-[(9-azabicyclo[3.3.1]nonan-9-yl)methyl]-5-(3,5-dibromo-2-methoxyphenyl)- 1H-pyrrole, 2-(3,5-dibromo-2-methoxyphenyl)-5-[1-(1-piperidinyl)propyl]-1H-pyrrole, 2-(N-cyclohexylmethyl-N-ethylaminomethyl)-5-(3,5-dibromo-2-methoxyphenyl)-1H-pyrrole, 2-[2-phenyl-1-(1-piperidinyl)ethyl]-5-(5-bromo-2,3-dimethoxyphenyl)-1H-pyrrole, 2-(5-ethylsulphonyl-2-methoxyphenyl)-5-[1-(1-piperidinyl)-ethyl]-1H-pyrrole, faster eluting enantiomer, and 2-(5-ethylsulphonyl-2-methoxyphenyl)-5-[1-(1-piperidinyl)-ethyl]-1H-pyrrole, slower eluting enantiomer, 2-(5-ethylsulfonyl-2-methoxyphenyl)-5-(1-(1,2,3,6-tetrahydro-pyridinyl)methyl)-1H-pyrrole, 2-(5-ethylsulfonyl-2-methoxyphenyl)-5-(1-(1-(1,2,3,6-tetrahydropyridinyl))ethyl)-1H-pyrrole, 2-[(2-azabicyclo[3.2.1]octan-2-yl)methyl]-5-(5-ethylsulphonyl-2-methoxyphenyl)- 1H-pyrrole, 2-(5-ethylsulphonyl-2-methoxyphenyl)-5-[1-(1-pyrrolidinyl)-ethyl]-1H-pyrrole, 2-(5-ethylsulphonyl-2-methoxyphenyl)-5-[N-ethyl-N-(2-thienyl)methyl-aminomethyl]-1H-pyrrole, 2-(5-ethylsulphonyl-2-methoxyphenyl)-5-[N-ethyl-N-(2-furyl)methyl-aminomethyl]-1H-pyrrole, 2-(5-ethylsulphonyl-2-methoxyphenyl)-5-(N-benzyl-N-propyl-aminomethyl)-1H-pyrrole, 2-(3-bromo-5-ethylsulphonyl-2-methoxyphenyl)-5-[N-ethyl-N-(4-methoxyphenyl)methyl-aminomethyl]-1H-pyrrole, 2-(5-ethylsulphonyl-2-methoxyphenyl)-5-[N-ethyl-N-(4-methoxyphenyl)methylaminomethyl]-1H-pyrrole, 2-(5-dimethylsulphamoyl-2-methoxyphenyl)-5-[1-(piperidinyl)]methyl-1H-pyrrole, 2-[(2-azabicyclo[2.2.1]heptan-2-yl)methyl]-5-(5-ethylsulphonyl-2-methoxyphenyl)- 1H-pyrrole, 2-[(2-azabicyclo[2.2.1]hept-5-en-2-yl)methyl]-5-(5-ethylsulphonyl- 2-methoxyphenyl)-1H-pyrrole, 2-[(2-azabicyclo[3.2.1]oct-6-en-2-yl)methyl]-5-(5-ethylsulphonyl- 2-methoxyphenyl)-1H-pyrrole, 2-(2-methoxy-5-methylsulphonylphenyl)-5-(1-piperidinylmethyl)-1H-pyrrole, 2-(2,3-dimethoxy-5-ethylsulphonylphenyl)-5-(1-piperidinylmethyl)-1H-pyrrole, 2-[(3-azabicyclo[3.2.1]octan-3-yl)methyl]-5-(5-ethylsulphonyl-2-methoxyphenyl)- 1H-pyrrole, 2-(5-ethylsulphonyl-2-methoxyphenyl)-5-[N-ethyl-N-[1-( 1,2,3,4-tetrahydro)naphthyl]aminomethyl]-1H-pyrrole, 2-(2-ethyl-2-azabicyclo[2.2.1]heptan-3-yl)-5-(5-ethylsulphonyl-2-methoxyphenyl)- 1H-pyrrole, 2-[1-(2-azabicyclo[2.2.1]heptan-2-yl)ethyl]-5-(5-ethylsulphonyl- 2-methoxyphenyl)-1H-pyrrole, 2-(5-ethylsulphonyl-2-methoxyphenyl)-5-[N-ethyl-N-(1-naphthyl)methyl-aminomethyl]-1H-pyrrole, 2-(5-isopropylsulphonyl-2-methoxyphenyl)-5-(1-piperidinylmethyl)-1H-pyrrole, (±)trans-2-(5-ethylsulphonyl-2-methoxyphenyl)-5-(perhydroisoquinolinylmethyl)-1H-pyrrole, or a pharmaceutically acceptable salt thereof.

8. A method of treating a condition which requires modulation of the dopamine $D_3$ receptor which comprises administering to a subject in need thereof an effective amount of a compound of formula (I) according to claim 14 or a physiologically acceptable salt thereof.

9. A method according to claim 8 wherein a dopamine antagonist is required.

10. A method according to claim 9 wherein the condition is a psychotic condition.

11. A pharmaceutical composition comprising a compound of formula (I) according to claim 1 or a physiologically acceptable salt thereof and a physiologically acceptable carrier.

12. A compound according to claim 1 wherein $R^1$ represents methyl, ethyl, or isopropyl; at least one of $R^2$ to $R^5$ is hydrogen, and the other substituents are selected from halogen, $C_{1-2}$alkyl, $C_{1-2}$alkoxy, $C_{1-2}$alkylsulphonyl, phenylsulphonyl, $CF_3$, $CF_3O$ and dialkylaminosulphonyl; and Y represents a group (a) in which $R^6$ represents hydrogen, $R^7$ represents hydrogen or methyl, $R^8$ represents $C_{1-4}$alkyl and $R^9$ represents $C_{1-4}$alkyl, cyclopropylmethyl, allyl or optionally substituted phenylmethyl; or -$NR^8R^9$ forms a fully or partially saturated 5 to 8 membered heterocyclic ring, optionally including a $C_{1-3}$alkylene bridge; or a pharmaceutically acceptable salt thereof.

13. A compound according to claim 1 wherein $R^1$ represents methyl, ethyl, or isopropyl;

at least one of $R^2$ to $R^5$ is hydrogen, and the other substituents are selected from halogen, $C_{1-2}$alkyl, $C_{1-2}$alkoxy, $C_{1-2}$alkylsulphonyl, phenylsulphonyl, $CF_3$, $CF_3O$ and dialkylaminosulphonyl; and Y represents a group (b) in which $R^{10}$ represents $C_{1-4}$alkyl, cyclopropylmethyl, allyl or benzyl; or a pharmaceutically acceptable salt thereof.

* * * * *